United States Patent
Naoe et al.

(10) Patent No.: US 9,987,278 B2
(45) Date of Patent: *Jun. 5, 2018

(54) PHARMACEUTICAL COMPOSITION FOR TREATING FLT3 MUTATION-POSITIVE CANCER, MUTANT FLT3 INHIBITOR AND USES THEREOF

(71) Applicant: FUJIFILM Corporation, Tokyo (JP)

(72) Inventors: Tomoki Naoe, Nagoya (JP); Hitoshi Kiyoi, Nagoya (JP); Shinji Hagiwara, Ashigarakami-gun (JP); Masaru Takasaki, Ashigarakami-gun (JP); Daisuke Hirano, Ashigarakami-gun (JP); Toshiyuki Nakatani, Ashigarakami-gun (JP); Takeshi Yamaura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/436,037

(22) Filed: Feb. 17, 2017

(65) Prior Publication Data

US 2017/0165262 A1    Jun. 15, 2017

Related U.S. Application Data

(63) Continuation of application No. PCT/JP2015/073688, filed on Aug. 24, 2015.

(30) Foreign Application Priority Data

Aug. 22, 2014 (JP) .................. 2014-169709
Sep. 3, 2014 (JP) .................. 2014-178737

(51) Int. Cl.
A61K 31/505 (2006.01)
A61K 31/506 (2006.01)
A61K 31/5377 (2006.01)

(52) U.S. Cl.
CPC .......... *A61K 31/506* (2013.01); *A61K 31/505* (2013.01); *A61K 31/5377* (2013.01)

(58) Field of Classification Search
CPC . A61K 31/505; A61K 31/506; A61K 31/5377
USPC .................................. 514/210.18
See application file for complete search history.

(56) References Cited

U.S. PATENT DOCUMENTS

| | | | |
|---|---|---|---|
| 8,703,767 B2 | 4/2014 | Bearss et al. | |
| 9,145,415 B2 * | 9/2015 | Takasaki ............. | C07D 403/12 |
| 9,701,644 B2 * | 7/2017 | Mizumoto ........... | C07D 239/48 |
| 2003/0171359 A1 | 9/2003 | Dahmann et al. | |
| 2012/0035168 A1 | 2/2012 | Brandl et al. | |
| 2012/0149722 A1 | 6/2012 | Lee et al. | |
| 2013/0059847 A1 | 3/2013 | Bearss et al. | |
| 2015/0045339 A1 | 2/2015 | Takasaki et al. | |

(Continued)

FOREIGN PATENT DOCUMENTS

| | | |
|---|---|---|
| CN | 102105150 A | 6/2011 |
| JP | 2009-515851 A | 4/2009 |
| WO | 91/09856 A1 | 7/1991 |

(Continued)

OTHER PUBLICATIONS

Keith W. Pratz et al., "FLT3-mutant allelic burden and clinical status are predictive of response to FLT3 inhibitors in AML", Blood, Feb. 18, 2010, vol. 115, No. 7, pp. 1425-1432 (9 pgs. total).
D. Gary Gilliland et al., "The roles of FLT3 in hematopoiesis and leukemia", Blood, Sep. 1, 2002, vol. 100, No. 5, pp. 1532-1542 (12 pgs. total).
P. Brown et al., "FLT3 Inhibitors: a paradigm for the development of targeted therapeutics for paediatric cancer", European Journal of Cancer, 2004, vol. 40, pp. 707-721 (18 pgs. total).
American Cancer Society, Cancer Facts & Figures, 2012, pp. 9-24 (68 pgs. total).
S. Yokota et al., "Internal tandem duplication of the FLT3 gene is preferentially seen in acute myeloid leukemia and myelodysplastic syndrome among various hematological malignancies. A study on a large series of patients and cell lines", Leukemia, 1997, vol. 11, pp. 1605-1609.

(Continued)

*Primary Examiner* — Yong Chu
(74) *Attorney, Agent, or Firm* — Sughrue Mion, PLLC

(57) ABSTRACT

Provided are a pharmaceutical composition for treating an FLT3 mutation-positive cancer; a mutant FLT3 inhibitor; and uses thereof. Disclosed are a pharmaceutical composition for treating an FLT3 mutation-positive cancer, containing a compound represented by General Formula [1] or a salt thereof as an active ingredient; a mutant FLT3 inhibitor; an anticancer agent; a method for predicting a therapeutic effect by administration of a pharmaceutical composition containing a compound represented by General Formula [1] or a salt thereof in a subject, including a step of detecting the presence or absence of an FLT3 mutation; a method for selecting a subject to whom a pharmaceutical composition containing a compound represented by General Formula [1] or a salt thereof is applied, including a step of detecting the presence or absence of an FLT3 mutation; and a method for determining whether or not a pharmaceutical composition containing a compound represented by General Formula [1] or a salt thereof is administered to a subject, including a step of detecting the presence or absence of an FLT3 mutation.

[1]

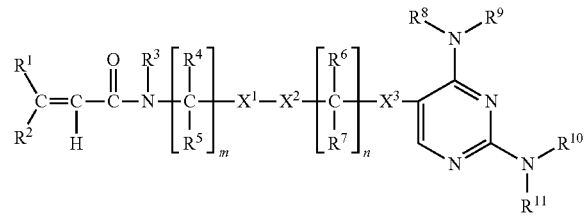

18 Claims, 1 Drawing Sheet

(56) References Cited

U.S. PATENT DOCUMENTS

2015/0225436 A1 8/2015 Wang et al.
2016/0229812 A1 8/2016 Mizumoto et al.

FOREIGN PATENT DOCUMENTS

| WO | 2006/133426 A2 | 12/2006 |
|---|---|---|
| WO | 2006/135713 A2 | 12/2006 |
| WO | 2007/054550 A1 | 5/2007 |
| WO | 2007/109120 A2 | 9/2007 |
| WO | 2009/095399 A2 | 8/2009 |
| WO | 2010/129053 A2 | 11/2010 |
| WO | 2012/061303 A1 | 5/2012 |
| WO | 2012/064706 A1 | 5/2012 |
| WO | 2012/135801 A1 | 10/2012 |
| WO | 2012/150952 A1 | 11/2012 |
| WO | 2013/157540 A1 | 10/2013 |
| WO | 2015/056683 A1 | 4/2015 |

OTHER PUBLICATIONS

Chunaram Choudhary et al., "AML-associated Flt3 kinase domain mutations show signal transduction differences compared with Flt3 ITD mutations", Blood, Jul. 1, 2005, vol. 106, No. 1, pp. 265-273.
Hitoshi Kiyoi et al., "Mechanism of constitutive activation of FLT3 with internal tandem duplication in the juxtamembrane domain", Oncogene, 2002, vol. 21, pp. 2555-2563.
CAS Registry Nos. 1208542-16-8; 1211912-67-2; and 1370823-68-9, 2 pgs. total (2010).
Jacques H. Poupaert, "Drug Design: Basic Principles and Applications", in 2 Encyclopedia of Pharmaceutical Technology, pp. 1362-1370 (James Swarbrick ed., 3rd ed., 2007).
Bruce A. Chabner et al., Chemotherapy of Neoplastic Diseases, "Antineoplastic Agents," Goodman & Gilman's: The Pharmacological Basis of Therapeutics, Chapter 51, pp. 1315-1403 (L.L. Brunton et al., eds., 11th ed., 2006) (93 pgs. total).
Jan Cools et al., Prediction of Resistance to Small Molecule FLT3 Inhibitors: Implications for Molecularly Targeted Therapy of Acute Leukemia, Cancer Research, vol. 64, Sep. 15, 2004, pp. 6385-6389 (6 pgs. total).
Andrica C.H. de Vries et al., "Role of mutation independent constitutive activation of FLT3 in juvenile myelomonocytic leukemia", Haematologica, 2007, vol. 92, No. 11, pp. 1557-1560.
International Search Report dated Oct. 13, 2015, issued by the International Searching Authority in corresponding Application No. PCT/JP2015/073688.
International Preliminary Report on Patentability with translation of Written Opinion dated Mar. 9, 2017, issued by the International Bureau in corresponding Application No. PCT/JP2015/073688.
International Search Report with Written Opinion dated Dec. 22, 2014, issued by the International Searching Authority in International Application No. PCT/JP2014/077368 (published as WO 2015/056683 A1).
Serajuddin, "Salt formation to improve drug solubility", Advanced Drug Delivery Reviews 59 (2007), pp. 603-616.
Bastin et al., "Salt Selection and Optimisation Procedures for Pharmaceutical New Chemical Entities", Organic Process Research & Development 2000, vol. 4, No. 5, pp. 427-435.
Liu, Rong, ed., Water-Insoluble Drug Formation (CRC Press, 2008) Chapter 15 pp. 417-435.
Morris et al., "An integrated approach to the selection of optimal salt form for a new drug candidate", International Journal of Pharmaceutics 105 (1994), pp. 209-217.

Adeyeye, Moji, ed., Preformulation in Solid Dosage Form Development (Informa Healthcare, 2008) Chapter 2.3, pp. 63-80.
Swarbrick et al., eds. Encyclopedia of Pharmaceutical Technology 13 (Marcel Dekker, NY 1996) pp. 453-499.
Gould, "Salt selection for basic drugs", International Journal of Pharmaceutics, 33 (1986), pp. 201-217.
International Preliminary Report on Patentability with translation of Written Opinion dated Apr. 28, 2016, issued by the International Bureau in International Application No. PCT/JP2014/077368.
Extended European Search Report dated Jul. 26, 2017, from the European Patent Office in counterpart European Application No. 15833175.1.
H. Quentmeier et al., "FLT3 mutations in acute myeloid leukemia cell lines", Leukemia (2003) vol. 17, Nature Publishing Group, 120-124 (5 pages total).
Office Action dated Dec. 29, 2017, from the Patent Office, Intellectual Property India in related Indian Application No. 8285/CHENP/2014.
Communication dated Sep. 9, 2015 from the United States Patent and Trademark Office in U.S. Appl. No. 14/516,337.
Corrected Notice of Allowance dated Sep. 8, 2015, which issued during the prosecution of U.S. Appl. No. 14/516,337.
Notice of Allowance dated May 8, 2015, which issued during the prosecution of U.S. Appl. No. 14/516,337.
Communication dated Dec. 9, 2014 from the United States Patent and Trademark Office in U.S. Appl. No. 14/516,337.
Communication dated Aug. 26, 2015 from the European Patent Office in EP Application No. 13778349.4.
Communication dated Jul. 3, 2015 from the State Intellectual Property Office of the P.R.C. in Chinese Application No. 201380020639.X.
de Vries et al., "Role of Mutation Independent Constitutive Activation of FLT3 in Juvenile Myelomonocytic Leukemia," Haematologica/the Hematology Journal, vol. 92, No. 11, 2007, pp. 1557-1560.
International Search Report dated Jun. 4, 2013 issued in PCT/JP2013/061273.
International Preliminary Report on Patentability dated Oct. 30, 2014 in International Application No. PCT/JP2013/061273.
Communication dated Nov. 18, 2016 from the United States Patent and Trademark Office in U.S. Appl. No. 15/130,168.
Notice of Allowance dated Mar. 10, 2017, which issued during the prosecution of U.S. Appl. No. 15/130,168.
Corrected Notice of Allowance dated May 23, 2017, which issued during the prosecution of U.S. Appl. No. 15/130,168.
Communication dated Jun. 21, 2017 from the United States Patent and Trademark Office in U.S. Appl. No. 15/130,168.
Communication dated Mar. 22, 2017 from the State Intellectual Property Office of the P.R.C. in Application No. 201480056478.4.
Communication dated Aug. 9, 2016 from the European Patent Office in Application No. 14854750.8.
Written Opinion dated Jun. 4, 2013 issued in PCT/JP2013/061273.
Office Action dated Aug. 29, 2017, from Japanese Patent Office in counterpart Japanese Application No. 2016-544276.
Yao, Qing et al., "FLT3 Expressing Leukemias Are Selectively Sensitive to Inhibitors of the Molecular Chaperone Heat Shock Protein 90 through Destabilization of Signal Transduction-Associated Kinases," Clinical Cancer Research, Oct. 1, 2003, vol. 9, No. 12, p. 4483-4493.
Office Action dated Apr. 23, 2018 issued by the European Patent Office in European Patent Application No. 14854750.8.

* cited by examiner

FLT3 (SEQ ID NO.:1)
```
  1 mpalardggq lpllvvfsam ifgtitnqdl pvikcvlinh knndssvgks ssypmvsesp
 61 edlgcalrpq ssgtvyeaaa vevdvsasit lqvlvdapgn isclwvfkhs slncqphfdl
121 qnrgvvsmvi lkmtetqage yllfiqseat nytilftvsi rntllytlrr pyfrkmenqd
181 alvcisesvp epivewvlcd sqgesckees pavvkkeekv lhelfgtdir ccarnelgre
241 ctrlftidln qtpqttlpql flkvgeplwi rckavhvnhg fgltwelenk aleegnyfem
301 stystnrtmi rilfafvssv arndtgyytc ssskhpsqsa lvtivekgfi natnssedye
361 idqyeefcfs vrfkaypqir ctwtfsrksf pceqkgldng ysiskfcnhk hqpgeyifha
421 enddaqftkm ftlnirrkpq vlaeasasqa scfsdgyplp swtwkkcsdk spncteeite
481 gvwnrkanrk vfgqwvssst lnmseaikgf lvkccaynsl gtscetilln spgpfpfiqd
541 nisfyatigv cllfivvltl lichkykkqf ryesqlqmvq vtgssdneyf yvdfreyeyd
601 lkwefprenl efgkvlgsga fgkvmnatay gisktgvsiq vavkmlkeka dsserealms
661 elkmmtqlgs henivnllga ctlsgpiyli feyccygdll nylrskrekf hrtwteifke
721 hnfsfyptfq shpnssmpgs revqihpdsd qisglhgnsf hsedeieyen qkrleeeedl
781 nvltfedllc fayqvakgme flefkscvhr dlaarnvlvt hgkvvkicdf glardimsds
841 nyvvrgnarl pvkwmapesl fegiytiksd vwsygillwe ifslgvnpyp gipvdanfyk
901 liqngfkmdq pfyateeiyi imqscwafds rkrpsfpnlt sflgcqlada eeamyqnvdg
961 rvsecphtyq nrrpfsremd lgllspqaqv eds
```

PHARMACEUTICAL COMPOSITION FOR TREATING FLT3 MUTATION-POSITIVE CANCER, MUTANT FLT3 INHIBITOR AND USES THEREOF

CROSS REFERENCE OF THE RELATED APPLICATIONS

This application is a Continuation of PCT International Application No. PCT/JP2015/073688 filed on Aug. 24, 2015, which claims priority under 35 U.S.C. 119(a) to Japanese Patent Application Nos. 2014-169709 and 2014-178737 filed on Aug. 22, 2014 and Sep. 3, 2014, respectively. Each of the above applications is hereby expressly incorporated by reference, in its entirety, into the present application.

BACKGROUND OF THE INVENTION

1. Field of the Invention

The present invention relates to a pharmaceutical composition for treating an Fms-like tyrosine kinase 3 (FLT3) mutation-positive cancer, containing a nitrogen-containing heterocyclic compound or a salt thereof as an active ingredient, a mutant FLT3 inhibitor, and uses thereof.

2. Description of the Related Art

The Fms-like tyrosine kinase 3 (FLT3) is a protein belonging to the class III of receptor tyrosine kinases and has five immnunoglobulin-like motifs in the N-terminal extracellular domain and two kinase domains at the C-terminal. FLT3 is expressed on normal CD34-positive human bone marrow progenitor cells and dendritic progenitor cells and plays an important role in growth, differentiation or the like of these cells (Brown P, et al., European Journal of Cancer, Vol. 40, pp. 707 to 721, 2004). In addition, the ligand of FLT3 (FL) is one of cytokines that is expressed in bone marrow stroma cells and T cells to thereby have an effect on development of a number of hematopoietic lineage cells and stimulate growth of stem cells, progenitor cells, dendritic cells and natural killer cells through interactions with other growth factors.

FLT3 dimerizes when FL binds thereto, and then is activated by autophosphorylation. As a result, phosphorylation of AKT and ERK of PI3 and RAS signaling pathways is induced. FLT3 plays an important role in growth and differentiation of hematopoietic cells.

In normal bone marrow, the expression of FLT3 is limited to early progenitor cells, but in blood cancer, FLT3 is expressed at high levels or FLT3 undergoes gene mutation, thereby contributing to malignant growth of cancer through the activation of the signaling pathways. Examples of the blood cancer include acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large cell lymphoma (ALCL), prolymphocytic leukemia (PML), juvenile myelomonocytic leukemia (JMML), adult T cell ALL, myelodysplastic syndrome (MDS) and myeloproliferative disease (MPD).

Although several existing therapies exhibit successful results to some extent against AML among blood cancers, AML shows relapse and resistance in many cases and is therefore still refractory cancer with a 5-year survival rate of about 24% (in the United States) (American Cancer Society, Cancer Facts and Figures, pp. 9 to 24, 2012). One of causes for the relapse and resistance is genetic mutations of AML cells, among which a mutation of the FLT3 gene has been identified most frequently. Examples of FLT3 gene mutations include an Internal Tandem Duplication (ITD) mutation where a portion of the juxtamembrane domain is repeated, and a TKD mutation where amino acid residues located in the Tyrosine Kinase Domain (TKD) are changed to different amino acid residues by substitution, deletion or addition (American Cancer Society, Cancer Facts and Figures, pp. 9 to 24, 2012), and it is known that FLT3 is constitutively activated even in the absence of a ligand, thereby enhancing the growth of cancer cells.

Since the ITD mutation is known as a poor prognostic factor in AML, improvements of prognosis by existing chemotherapies have been attempted but there has been a difficulty therein. From such a situation, the NCCN Guidelines for the treatment of AML specify that participation in a clinical trial which can be the subject should be taken into account as one of treatment options. Further, also in the WHO classification 4th edition, the ITD mutation has been described as one of genetic mutations to be screened for diagnosis and treatment of AML.

The TKD mutation is known to show mutations or deletions of aspartic acid residue 835 (D835) and surrounding amino acid residues located particularly in the activation loop in AML, and there are also some reports that the TKD mutation is a poor prognostic factor. In addition, mutations of phenylalanine residue 691 (F691) and surrounding amino acid residues located in the gatekeeper domain known as one of the drug resistance mechanisms in other tyrosine kinases have also been recognized as the TKD mutation. In clinical trials for the treatment of AML by an FLT3-targeting drug, drug resistance of AML having both the ITD mutation and the TKD mutation is already known.

Since it is considered that inhibition of the activity of mutant FLT3, together with inhibition of the activity of FLT3, is important for the treatment and prognostic improvement of AML, the development of a pharmaceutical agent inhibiting FLT3 and mutant FLT3 have been conducted. For example, AC220 (Ambit Inc.) is a compound that selectively inhibits type III tyrosine kinases (FLT3, c-KIT, FMS, and PDGFR), and the development of a pharmaceutical agent that targets AML has been conducted (WO2007/109120A). However, there is no report for a pharmaceutical agent that sufficiently inhibits the activity of mutant FLT3.

On the other hand, a nitrogen-containing heterocyclic compound or a salt thereof described in WO2013/157540A has been known as an FLT3 inhibitor.

SUMMARY OF THE INVENTION

An object of the present invention is to provide a pharmaceutical composition for treating an FLT3 mutation-positive cancer, a mutant FLT3 inhibitor, and uses thereof.

A compound which is a specific nitrogen-containing heterocyclic compound or a salt thereof and is effective in a case where mutant FLT3, particularly a TKD mutation is observed has not been known. The present invention provides the following.

[1] A pharmaceutical composition for treating an FLT3 mutation-positive cancer, comprising a compound represented by General Formula [1]:

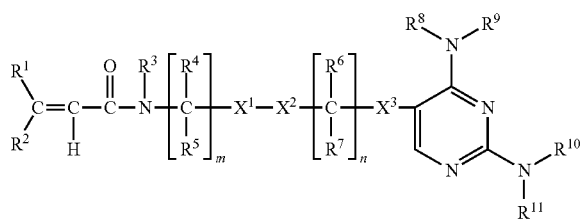

in the formula,

R¹ represents a hydrogen atom or a $C_{1-6}$ alkyl group which may be substituted, R² represents a hydrogen atom, a $C_{1-6}$ alkyl group which may be substituted, a $C_{2-6}$ alkenyl group which may be substituted or a $C_{2-6}$ alkynyl group which may be substituted, R³ represents a hydrogen atom, a $C_{1-6}$ alkyl group which may be substituted, a $C_{2-6}$ alkenyl group which may be substituted or a $C_{2-6}$ alkynyl group which may be substituted, m represents an integer of 1 to 3, m number of R⁴'s are the same or different and represent a hydrogen atom or a $C_{1-6}$ alkyl group which may be substituted, and one R⁴ selected from m number of R⁴'s together with R³ may form a $C_{1-6}$ alkylene group which may be substituted, m number of R⁵'s are the same or different and represent a hydrogen atom or a $C_{1-6}$ alkyl group which may be substituted, a $C_{2-6}$ alkenyl group which may be substituted or a $C_{2-6}$ alkynyl group which may be substituted, X¹ represents an oxygen atom, N(R²⁰) (in the formula, R²⁰ represents a hydrogen atom, a $C_{1-6}$ alkyl group which may be substituted, a $C_{2-6}$ alkenyl group which may be substituted or a $C_{2-6}$ alkynyl group which may be substituted), C(=O), C(=O)—N(R²⁰) (in the formula, R²⁰ has the same meaning as defined above) or a bond, X² represents a $C_{1-6}$ alkylene group which may be substituted, a divalent alicyclic hydrocarbon group which may be substituted or a divalent aromatic hydrocarbon group which may be substituted, n represents an integer of 0 to 3, n number of R⁶'s are the same or different and represents a hydrogen atom or a $C_{1-6}$ alkyl group which may be substituted, n number of R⁷'s are the same or different and represent a hydrogen atom or a $C_{1-6}$ alkyl group which may be substituted, X³ represents a $C_{1-6}$ alkylene group which may be substituted, a $C_{2-6}$ alkenylene group which may be substituted, a $C_{2-6}$ alkynylene group which may be substituted or N(R²⁰)—C(=O) (in the formula, R²⁰ has the same meaning as defined above), R⁸ represents a hydrogen atom, a $C_{1-6}$ alkyl group which may be substituted, a $C_{2-6}$ alkenyl group which may be substituted or a $C_{2-6}$ alkynyl group which may be substituted, R⁹ represents a $C_{1-6}$ alkyl group which may be substituted, a $C_{2-6}$ alkenyl group which may be substituted, a $C_{2-6}$ alkynyl group which may be substituted or a $C_{3-8}$ cycloalkyl group which may be substituted, R⁸ and R⁹, together with the nitrogen atom to which they are bonded, may form a cyclic amino group which may be substituted, R¹⁰ represents a hydrogen atom, a $C_{1-6}$ alkyl group which may be substituted, a $C_{2-6}$ alkenyl group which may be substituted or a $C_{2-6}$ alkynyl group which may be substituted, and R¹¹ represents a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted or a heterocyclic group which may be substituted; or a salt thereof.

[2] The pharmaceutical composition according to [1], in which R¹⁰ is a hydrogen atom.

[3] The pharmaceutical composition according to [1] or [2], in which X¹ is C(=O)—N(R²⁰) (in the formula, R²⁰ represents a hydrogen atom, a $C_{1-6}$ alkyl group which may be substituted, a $C_{2-6}$ alkenyl group which may be substituted or a $C_{2-6}$ alkynyl group which may be substituted).

[4] The pharmaceutical composition according to any one of [1] to [3], in which X³ is a $C_{2-6}$ alkynylene group which may be substituted.

[5] The pharmaceutical composition according to any one of [1] to [4], in which the FLT3 mutation includes a TKD mutation.

[6] The pharmaceutical composition according to [5], in which the TKD mutation is mutation(s) of one or plural amino acids in the amino acids 823 to 861 region in the amino acid sequence of SEQ ID NO: 1.

[7] The pharmaceutical composition according to [6], in which the TKD mutation is a mutation of at least one amino acid selected from the group consisting of amino acids 835, 836 and 842 in the amino acid sequence of SEQ ID NO: 1.

[8] The pharmaceutical composition according to [7], in which the TKD mutation is at least one selected from the group consisting of the following:

a. a substitution of aspartic acid 835 in the amino acid sequence of SEQ ID NO: 1 to valine, tyrosine, histidine, glutamic acid or asparagine;

b. a substitution of isoleucine 836 in the amino acid sequence of SEQ ID NO: 1 to leucine-aspartic acid; and c. a substitution of tyrosine 842 in the amino acid sequence of SEQ ID NO: 1 to cysteine or histidine.

[9] The pharmaceutical composition according to [5], in which the TKD mutation is mutation(s) of one or plural amino acids in the amino acids 604 to 822 region in the amino acid sequence of SEQ ID NO: 1.

[10] The pharmaceutical composition according to [9], in which the TKD mutation is a mutation of at least one amino acid selected from the group consisting of amino acids 621, 627, 676, 691 and 697 in the amino acid sequence of SEQ ID NO: 1.

[11] The pharmaceutical composition according to [10], in which the TKD mutation is a mutation of amino acid 691 in the amino acid sequence of SEQ ID NO: 1.

[12] The pharmaceutical composition according to [11], in which the mutation of amino acid 691 in the amino acid sequence of SEQ ID NO: 1 is a substitution of phenylalanine to leucine.

[13] The pharmaceutical composition according to any one of [5] to [12], in which the FLT3 mutation further includes an ITD mutation.

[14] A mutant FLT3 inhibitor comprising the compound or the salt thereof as defined in any one of [1] to [4].

[15] The inhibitor according to [14], which inhibits mutant FLT3 containing a TKD mutation.

[16] The inhibitor according to [15], which inhibits mutant FLT3 further containing an ITD mutation.

[17] The inhibitor according to any one of [14] to [16], which further inhibits wild-type FLT3.

[18] The inhibitor according to any one of [14] to [17], which is an anticancer agent.

[19] A method for predicting a therapeutic effect by administration of a pharmaceutical composition including the compound or the salt thereof as defined in any one of [1] to [4] in a subject, comprising a step of detecting the presence or absence of an FLT3 mutation.

[20] A method for selecting a subject to whom a pharmaceutical composition including the compound or the salt thereof as defined in any one of [1] to [4] is applied, comprising a step of detecting the presence or absence of an FLT3 mutation.

[21] A method for determining whether or not a pharmaceutical composition including the compound or the salt thereof as defined in any one of [1] to [4] is administered to a subject, comprising a step of detecting the presence or absence of an FLT3 mutation.

[22] The method according to any one of [19] to [21], in which the FLT3 mutation includes a TKD mutation.

[23] The method according to any one of [19] to [22], in which the FLT3 mutation further includes an ITD mutation.

[1a] A method for treating an FLT3 mutation-positive cancer in a subject, comprising a step of administering the compound or the salt thereof as defined in any one of [1] to [4] to the subject.

[2a] The method according to [1a], in which the FLT3 mutation includes a TKD mutation.

[3a] The method according to [2a], in which the TKD mutation is mutation(s) of one or plural amino acids in the amino acids 823 to 861 region in the amino acid sequence of SEQ ID NO: 1.

[4a] The method according to [3a], in which the TKD mutation is a mutation of at least one amino acid selected from the group consisting of amino acids 835, 836 and 842 in the amino acid sequence of SEQ ID NO: 1.

[5a] The method according to [4a], in which the TKD mutation is at least one selected from the group consisting of the following:

a. a substitution of aspartic acid 835 in the amino acid sequence of SEQ ID NO: 1 to valine, tyrosine, histidine, glutamic acid or asparagine;

b. a substitution of isoleucine 836 in the amino acid sequence of SEQ ID NO: 1 to leucine-aspartic acid; and c. a substitution of tyrosine 842 in the amino acid sequence of SEQ ID NO: 1 to cysteine or histidine.

[6a] The method according to [2a], in which the TKD mutation is mutation(s) of one or plural amino acids in the amino acids 604 to 822 region in the amino acid sequence of SEQ ID NO: 1.

[7a] The method according to [6a], in which the TKD mutation is a mutation of at least one amino acid selected from the group consisting of amino acids 621, 627, 676, 691 and 697 in the amino acid sequence of SEQ ID NO: 1.

[8a] The method according to [7a], in which the TKD mutation is a mutation of amino acid 691 in the amino acid sequence of SEQ ID NO: 1.

[9a] The method according to [8a], in which the mutation of amino acid 691 in the amino acid sequence of SEQ ID NO: 1 is a substitution of phenylalanine to leucine.

[10a] The method according to any one of [1a] to [8a], in which the FLT3 mutation further includes an ITD mutation.

[1b] The compound or the salt thereof as defined in any one of [1] to [4] for use in a method for treating an FLT3 mutation-positive cancer.

[2b] The compound or the salt thereof according to [1b], in which the FLT3 mutation includes a TKD mutation.

[3b] The compound or the salt thereof according to [2b], in which the TKD mutation is mutation(s) of one or plural amino acids in the amino acids 823 to 861 region in the amino acid sequence of SEQ ID NO: 1.

[4b] The compound or the salt thereof according to [3b], in which the TKD mutation is a mutation of at least one amino acid selected from the group consisting of amino acids 835, 836 and 842 in the amino acid sequence of SEQ ID NO: 1.

[5b] The compound or the salt thereof according to [4b], in which the TKD mutation is at least one selected from the group consisting of the following:

a. a substitution of aspartic acid 835 in the amino acid sequence of SEQ ID NO: 1 to valine, tyrosine, histidine, glutamic acid or asparagine;

b. a substitution of isoleucine 836 in the amino acid sequence of SEQ ID NO: 1 to leucine-aspartic acid;

c. a substitution of tyrosine 842 in the amino acid sequence of SEQ ID NO: 1 to cysteine or histidine.

[6b] The compound or the salt thereof according to [2b], in which the TKD mutation is mutation(s) of one or plural amino acids in the amino acids 604 to 822 region in the amino acid sequence of SEQ ID NO: 1.

[7b] The compound or the salt thereof according to [6b], in which the TKD mutation is a mutation of at least one amino acid selected from the group consisting of amino acids 621, 627, 676, 691 and 697 in the amino acid sequence of SEQ ID NO: 1.

[8b] The compound or the salt thereof according to [7b], in which the TKD mutation is a mutation of amino acid 691 in the amino acid sequence of SEQ ID NO: 1.

[9b] The compound or the salt thereof according to [8b], in which the mutation of amino acid 691 in the amino acid sequence of SEQ ID NO: 1 is a substitution of phenylalanine to leucine.

[10b] The compound or the salt thereof according to any one of [1b] to [8b], in which the FLT3 mutation further includes an ITD mutation.

A compound represented by General Formula [1] or a salt thereof has an inhibitory activity on growth and phosphorylation of an FLT3 mutation-positive cell line and an FLT3 mutation-expressing cell line. Accordingly, the compound represented by General Formula [1] or the salt thereof can be used as a pharmaceutical composition for treating an FLT3 mutation-positive cancer or a mutant FLT3 inhibitor.

BRIEF DESCRIPTION OF THE DRAWINGS

FIG. 1 is an amino acid sequence of SEQ ID NO: 1.

DESCRIPTION OF THE PREFERRED EMBODIMENTS

Hereinafter, the present invention will be described in detail.

In the present invention, unless otherwise indicated, individual terms have the following meanings.

The treatment refers to prevention, treatment, or the like.

The prevention refers to inhibition of disease onset, reduction of disease onset risk, delay of disease onset, or the like.

The treating refers to improvement of, or inhibition of progression (maintenance or delay) of a target disease or condition.

The subject refers to a mammal including a human, or the like.

In a case where a range is given with the expression of "a to b", the range includes values a and b at both ends.

The halogen atom refers to a fluorine atom, a chlorine atom, a bromine atom or an iodine atom.

The $C_{1-6}$ alkyl group refers to a linear or branched $C_{1-6}$ alkyl group such as a methyl, ethyl, propyl, isopropyl, butyl, sec-butyl, isobutyl, tert-butyl, pentyl, isopentyl or hexyl group.

The $C_{1-3}$ alkyl group refers to a methyl, ethyl, propyl or isopropyl group.

The $C_{2-6}$ alkenyl group refers to a linear or branched $C_{2-6}$ alkenyl group such as a vinyl, allyl, propenyl, isopropenyl, butenyl, isobutenyl, 1,3-butadienyl, pentenyl or hexenyl group.

The $C_{2-6}$ alkynyl group refers to a linear or branched $C_{2-6}$ alkynyl group such as an ethynyl, propynyl, butynyl, pentynyl or hexynyl group.

The $C_{3-8}$ cycloalkyl group refers to a $C_{3-8}$ cycloalkyl group such as a cyclopropyl, cyclobutyl, cyclopentyl or cyclohexyl group.

The aryl group refers to a phenyl or naphthyl group.

The Ar—$C_{1-6}$ alkyl group refers to an ar-$C_{1-6}$ alkyl group such as a benzyl, diphenylmethyl, trityl, phenethyl or naphthylmethyl group.

The $C_{1-6}$ alkoxy group refers to a linear, cyclic or branched $C_{1-6}$ alkyloxy group such as a methoxy, ethoxy, propoxy, isopropoxy, cyclopropoxy, butoxy, isobutoxy, sec-butoxy, tert-butoxy, cyclobutoxy, pentyloxy or hexyloxy group.

The $C_{1-3}$ alkoxy group refers to a methoxy, ethoxy, propoxy or isopropoxy group.

The $C_{1-6}$ alkoxy $C_{1-6}$ alkyl group refers to a $C_{1-6}$ alkyloxy $C_{1-6}$ alkyl group such as a methoxymethyl or 1-ethoxyethyl group.

The Ar—$C_{1-6}$ alkoxy $C_{1-6}$ alkyl group refers to an ar-$C_{1-6}$ alkyloxy $C_{1-6}$ alkyl group such as a benzyloxymethyl or phenethyloxymethyl group.

The $C_{2-6}$ alkanoyl group refers to a linear or branched $C_{2-6}$ alkanoyl group such as an acetyl, propionyl, valeryl, isovaleryl or pivaloyl group.

The aroyl group refers to a benzoyl or naphthoyl group.

The heterocyclic carbonyl group refers to a nicotinoyl, thenoyl, pyrrolidinocarbonyl or furoyl group.

The (α-substituted) aminoacetyl group refers to an (α-substituted) aminoacetyl group whose N-terminal derived from an amino acid (examples thereof include amino acids such as glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline and hydroxyproline) may be protected.

The acyl group refers to a formyl group, a succinyl group, a glutaryl group, a maleoyl group, a phthaloyl group, a $C_{2-6}$ alkanoyl group, an aroyl group, a heterocyclic carbonyl group or an (α-substituted) aminoacetyl group.

The acyl $C_{1-6}$ alkyl group refers to an acyl $C_{1-6}$ alkyl group such as an acetylmethyl, benzoylmethyl or 1-benzoylethyl group.

The acyloxy $C_{1-6}$ alkyl group refers to an acyloxy $C_{1-6}$ alkyl group such as an acetoxymethyl, propionyloxymethyl, pivaloyloxymethyl, benzoyloxymethyl or 1-(benzoyloxy)ethyl group.

The $C_{1-6}$ alkoxycarbonyl group refers to a linear or branched $C_{1-6}$ alkyloxycarbonyl group such as a methoxycarbonyl, ethoxycarbonyl, isopropoxycarbonyl, tert-butoxycarbonyl or 1,1-dimethylpropoxycarbonyl group.

The ar-$C_{1-6}$ alkoxycarbonyl group refers to an ar-$C_{1-6}$ alkyloxycarbonyl group such as a benzyloxycarbonyl or phenethyloxycarbonyl group.

The aryloxycarbonyl group refers to a phenyloxycarbonyl or naphthyloxycarbonyl group.

The $C_{1-6}$ alkylamino group refers to a linear or branched $C_{1-6}$ alkylamino group such as a methylamino, ethylamino, propylamino, isopropylamino, butylamino, sec-butylamino, tert-butylamino, pentylamino or hexylamino group.

The di($C_{1-6}$ alkyl)amino group refers to a linear or branched di($C_{1-6}$ alkyl)amino group such as a dimethylamino, diethylamino, dipropylamino, diisopropylamino, dibutylamino, di(tert-butyl)amino, dipentylamino, dihexylamino, (ethyl)(methyl)amino or (methyl)(propyl)amino group.

The di($C_{1-3}$ alkyl)amino group refers to a linear or branched di($C_{1-3}$ alkyl)amino group such as a dimethylamino, diethylamino, dipropylamino, diisopropylamino, (ethyl)(methyl)amino or (methyl)(propyl)amino group.

The $C_{1-6}$ alkylsulfonyl group refers to a $C_{1-6}$ alkylsulfonyl group such as a methylsulfonyl, ethylsulfonyl or propylsulfonyl group.

The arylsulfonyl group refers to a benzenesulfonyl, p-toluenesulfonyl or naphthalenesulfonyl group.

The $C_{1-6}$ alkylsulfonyloxy group refers to a $C_{1-6}$ alkylsulfonyloxy group such as a methylsulfonyloxy or ethylsulfonyloxy group.

The arylsulfonyloxy group refers to a benzenesulfonyloxy or p-toluenesulfonyloxy group.

The cyclic amino group refers to a cyclic amino group which contains one or more nitrogen atoms as hetero atoms forming a ring such as azetidinyl, pyrrolidinyl, pyrrolinyl, pyrrolyl, piperidinyl, tetrahydropyridyl, homopiperidinyl, imidazolidinyl, imidazolinyl, imidazolyl, pyrazolidinyl, pyrazolinyl, pyrazolyl, piperazinyl, homopiperazinyl, triazolyl, tetrazolyl, morpholinyl, thiomorpholinyl, tetrahydroquinolinyl, tetrahydroisoquinolinyl or quinuclidinyl and may further contain one or more oxygen atoms or sulfur atoms.

The monocyclic nitrogen-containing heterocyclic group refers to a monocyclic nitrogen-containing heterocyclic group which contains only nitrogen atoms as hetero atoms forming a ring such as an azetidinyl, pyrrolidinyl, pyrrolinyl, pyrrolyl, piperidyl, tetrahydropyridyl, pyridyl, homopiperidinyl, octahydroazocinyl, imidazolidinyl, imidazolinyl, imidazolyl, pyrazolidinyl, pyrazolinyl, pyrazolyl, piperazinyl, pyrazinyl, pyridazinyl, pyrimidinyl, homopiperazinyl, triazolyl or tetrazolyl group.

The monocyclic oxygen-containing heterocyclic group refers to a tetrahydrofuranyl, furanyl, tetrahydropyranyl or pyranyl group.

The monocyclic sulfur-containing heterocyclic group refers to a thienyl group.

The monocyclic nitrogen.oxygen-containing heterocyclic group refers to a monocyclic nitrogen.oxygen-containing heterocyclic group containing only nitrogen atoms and oxygen atoms as hetero atoms forming a ring such as an oxazolyl, isoxazolyl, oxadiazolyl or morpholinyl group The monocyclic nitrogen.sulfur-containing heterocyclic group refers to a monocyclic nitrogen.sulfur-containing heterocyclic group containing only nitrogen atoms and sulfur atoms as hetero atoms forming a ring such as a thiazolyl, isothiazolyl, thiadiazolyl, thiomorpholinyl, 1-oxide thiomorpholinyl or 1,1-dioxide thiomorpholinyl group.

The monocyclic heterocyclic group refers to a monocyclic nitrogen-containing heterocyclic group, a monocyclic oxygen-containing heterocyclic group, a monocyclic sulfur-containing heterocyclic group, a monocyclic nitrogen.oxygen-containing heterocyclic group or a monocyclic nitrogen.sulfur-containing heterocyclic group.

The bicyclic nitrogen-containing heterocyclic group refers to a bicyclic nitrogen-containing heterocyclic group containing only nitrogen atoms as hetero atoms forming a ring such as an indolinyl, indolyl, isoindolinyl, isoindolyl, benzimidazolyl, indazolyl, benzotriazolyl, pyrazolopyridinyl, quinolyl, tetrahydroquinolinyl, tetrahydroisoquinolinyl, isoquinolinyl, quinolizinyl, cinnolinyl, phthalazinyl, quinazolinyl, dihydroquinoxalinyl, quinoxalinyl, naphthyridinyl, purinyl, pteridinyl or quinuclidinyl group.

The bicyclic oxygen-containing heterocyclic group refers to a bicyclic oxygen-containing heterocyclic group containing only oxygen atoms as hetero atoms forming a ring such as a 2,3-dihydrobenzofuranyl, benzofuranyl, isobenzofuranyl, chromanyl, chromenyl, isochromanyl, 1,3-benzodioxalyl, 1,3-benzodioxanyl or 1,4-benzodioxanyl group.

The bicyclic sulfur-containing heterocyclic group refers to a bicyclic sulfur-containing heterocyclic group containing only sulfur atoms as hetero atoms forming a ring such as a 2,3-dihydrobenzothienyl or benzothienyl group.

The bicyclic nitrogen.oxygen-containing heterocyclic group refers to a bicyclic nitrogen.oxygen-containing heterocyclic group containing only nitrogen atoms and oxygen atoms as hetero atoms forming a ring such as a benzoxazolyl, benzisoxazolyl, benzoxadiazolyl, benzomorpholinyl, dihydropyranopyridyl, dihydrodioxynopyridyl or dihydropyridooxazinyl group.

The bicyclic nitrogen.sulfur-containing heterocyclic group refers to a bicyclic nitrogen.sulfur-containing heterocyclic group containing nitrogen atoms and sulfur atoms as hetero atoms forming a ring such as a benzothiazolyl, benzisothiazolyl or benzothiadiazolyl group.

The bicyclic heterocyclic group refers to a bicyclic nitrogen-containing heterocyclic group, a bicyclic oxygen-containing heterocyclic group, a bicyclic sulfur-containing heterocyclic group, a bicyclic nitrogen.oxygen-containing heterocyclic group or a bicyclic nitrogen.sulfur-containing heterocyclic group.

The heterocyclic group refers to a monocyclic heterocyclic group or a bicyclic heterocyclic group.

The $C_{1-6}$ alkylene group refers to a linear or branched $C_{1-6}$ alkylene group such as a methylene, ethylene, propylene, butylene or hexylene group.

The $C_{1-3}$ alkylene group refers to a methylene, ethylene or propylene group.

The $C_{2-6}$ alkenylene group refers to a linear or branched $C_{2-6}$ alkenylene group such as a vinylene, propenylene, butenylene or pentenylene group.

The $C_{2-6}$ alkynylene group refers to a linear or branched $C_{2-6}$ alkynylene group such as an ethynylene, propynylene, butynylene or pentynylene group.

The divalent alicyclic hydrocarbon group refers to a group formed by removing two hydrogen atoms from an alicyclic hydrocarbon ring such as a 1,2-cyclobutylene, 1,3-cyclobutylene, 1,2-cyclopentylene, 1,3-cyclopentylene, 1,2-cyclohexylene, 1,3-cyclohexylene, 1,4-cyclohexylene, bicyclo(3.2.1)octylene, bicyclo(2.2.0)hexylene or bicyclo(5.2.0)nonylene group.

The divalent aromatic hydrocarbon group refers to a group formed by removing two hydrogen atoms from an aromatic hydrocarbon ring such as a phenylene, indenylene, naphthylene, fluorenylene, phenanthrenylene, anthrylene or pyrenylene group.

The silyl group refers to a trimethylsilyl, triethylsilyl or tributylsilyl group.

The amino-protecting group is any conventional group which can be used as a protecting group of an amino group, and includes groups described in, for example, T. W. Greene et al., Protective Groups in Organic Synthesis 4th edition, pp. 696 to 926, 2007, John Wiley & Sons, INC. Specific examples of the amino-protecting group include an ar-$C_{1-6}$ alkyl group, a $C_{1-6}$ alkoxy $C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group, and a silyl group.

The imino-protecting group is any conventional group which can be used as a protecting group of an imino group, and includes groups described in, for example, T. W. Greene et al., Protective Groups in Organic Synthesis 4th edition, pp. 696 to 868, 2007, John Wiley & Sons, INC. Specific examples of the imino-protecting group include an ar-$C_{1-6}$ alkyl group, a $C_{1-6}$ alkoxy $C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group, and a silyl group.

The hydroxyl-protecting group is any conventional group which can be used as a protecting group of a hydroxyl group, and includes groups described in, for example, T. W. Greene et al., Protective Groups in Organic Synthesis 4th edition, pp. 16 to 299, 2007, John Wiley & Sons, INC. Specific examples of the hydroxyl-protecting group include a $C_{1-6}$ alkyl group, a $C_{2-6}$ alkenyl group, an ar-$C_{1-6}$ alkyl group, a $C_{1-6}$ alkoxy $C_{1-6}$ alkyl group, an ar-$C_{1-6}$ alkoxy $C_{1-6}$ alkyl group, an acyl group, a $C_{1-6}$ alkoxycarbonyl group, an ar-$C_{1-6}$ alkoxycarbonyl group, a $C_{1-6}$ alkylsulfonyl group, an arylsulfonyl group, a silyl group, a tetrahydrofuranyl group and a tetrahydropyranyl group.

The carboxyl-protecting group is any conventional group which can be used as a protecting group of a carboxyl group, and includes groups described in, for example, T. W. Greene et al., Protective Groups in Organic Synthesis 4th edition, pp. 533 to 643, 2007, John Wiley & Sons, INC. Specific examples of the carboxyl-protecting group include a $C_{1-6}$ alkyl group, a $C_{2-6}$ alkenyl group, an aryl group, an ar-$C_{1-6}$ alkyl group, a $C_{1-6}$ alkoxy $C_{1-6}$ alkyl group, an ar-$C_{1-6}$ alkoxy $C_{1-6}$ alkyl group, an acyl $C_{1-6}$ alkyl groups, an acyloxy $C_{1-6}$ alkyl group and a silyl group.

[Compound of General Formula [1] and salt thereof]

The nitrogen-containing heterocyclic compound in the present invention is a compound represented by General Formula [1]:

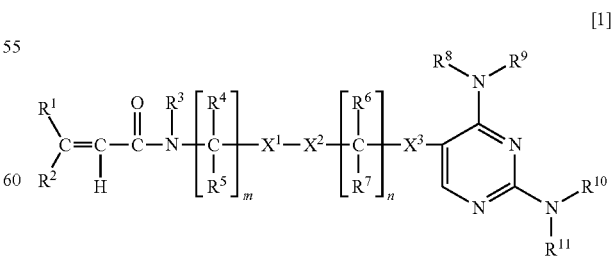

[1]

(in the formula, $R^1$, $R^2$, $R^3$, $R^4$, $R^5$, $R^6$, $R^7$, $R^8$, $R^9$, $R^{10}$, $R^{11}$, $X^1$, $X^2$, $X^3$, m and n have the same meaning as defined above).

$R^1$ is a hydrogen atom or a $C_{1-6}$ alkyl group which may be substituted, and preferably a hydrogen atom.

Even in a case where other substituents are of any kind, the $C_{1-6}$ alkyl group of $R^1$ may be substituted with one or more groups selected from a halogen atom, a cyano group, an amino group which may be protected and a hydroxyl group which may be protected.

The $C_{1-6}$ alkyl group in the $C_{1-6}$ alkyl group which may be substituted of $R^1$ is preferably a $C_{1-3}$ alkyl group.

$R^2$ is a hydrogen atom, a $C_{1-6}$ alkyl group which may be substituted, a $C_{2-6}$ alkenyl group which may be substituted or a $C_{2-6}$ alkynyl group which may be substituted, preferably a hydrogen atom or a $C_{1-6}$ alkyl group which may be substituted, and more preferably a $C_{1-6}$ alkyl group which may be substituted.

Even in a case where other substituents are of any kind, the $C_{1-6}$ alkyl group, $C_{2-6}$ alkenyl group or $C_{2-6}$ alkynyl group of $R^2$ may be substituted with one or more groups selected from a $C_{1-6}$ alkylamino group which may be substituted with one or more groups selected from Substituent Group A, a di($C_{1-6}$ alkyl)amino group which may be substituted with one or more groups selected from Substituent Group A and a heterocyclic group which may be substituted with one or more groups selected from Substituent Group A.

Substituent Group A: a halogen atom, a cyano group, an amino group which may be protected, a hydroxyl group which may be protected, a $C_{1-6}$ alkyl group which may be substituted with one or more groups selected from Substituent Group B, a $C_{3-8}$ cycloalkyl group which may be substituted with one or more groups selected from Substituent Group B, an aryl group which may be substituted with one or more groups selected from Substituent Group B, a $C_{1-6}$ alkoxy group which may be substituted with one or more groups selected from Substituent Group B, a $C_{1-6}$ alkylamino group which may be substituted with one or more groups selected from Substituent Group B, a di($C_{1-6}$ alkyl) amino group which may be substituted with one or more groups selected from Substituent Group B, a heterocyclic group which may be substituted with one or more groups selected from Substituent Group B, and an oxo group.

Substituent Group B: a halogen atom, a cyano group, an amino group which may be protected, a hydroxyl group which may be protected, a $C_{1-6}$ alkyl group which may be substituted with a halogen atom or a hydroxyl group, a $C_{1-6}$ alkoxy group which may be substituted with a halogen atom or a hydroxyl group, an aryl group, a heterocyclic group, and an oxo group.

The $C_{1-6}$ alkyl group which may be substituted of $R^2$ is preferably a $C_{1-6}$ alkyl group substituted with a di($C_{1-6}$ alkyl)amino group, more preferably a $C_{1-3}$ alkyl group substituted with a di($C_{1-3}$ alkyl)amino group, and still more preferably a dimethylaminomethyl group.

The $C_{1-6}$ alkyl group in the $C_{1-6}$ alkyl group which may be substituted of $R^2$ is preferably a $C_{1-3}$ alkyl group, and more preferably a methyl group.

Each of substituents of the $C_{1-6}$ alkyl group which may be substituted, $C_{2-6}$ alkenyl group which may be substituted or $C_{2-6}$ alkynyl group which may be substituted, of $R^2$, is preferably a di($C_{1-6}$ alkyl)amino group which may be substituted with one or more groups selected from Substituent Group A-1 or a heterocyclic group which may be substituted with one or more groups selected from Substituent Group A-1, and more preferably a di($C_{1-6}$ alkyl)amino group which may be substituted with one or more groups selected from Substituent Group A-1.

Here, the di($C_{1-6}$ alkyl)amino group in the di($C_{1-6}$ alkyl) amino group which may be substituted with one or more groups selected from Substituent Group A-1 is preferably a di($C_{1-3}$ alkyl)amino group, and more preferably a dimethylamino group.

The heterocyclic group in the heterocyclic group which may be substituted with one or more groups selected from Substituent Group A-1 is preferably an azetidinyl group, a piperazinyl group, or a morpholinyl group.

Substituent Group A-1: a halogen atom, a hydroxyl group which may be protected, and a $C_{1-6}$ alkyl group which may be substituted with a hydroxyl group.

$R^3$ is a hydrogen atom, a $C_{1-6}$ alkyl group which may be substituted, a $C_{2-6}$ alkenyl group which may be substituted or a $C_{2-6}$ alkynyl group which may be substituted, preferably a hydrogen atom or a $C_{1-6}$ alkyl group, and more preferably a $C_{1-6}$ alkyl group.

Even in a case where other substituents are of any kind, the $C_{1-6}$ alkyl group, $C_{2-6}$ alkenyl group or $C_{2-6}$ alkynyl group of $R^3$ may be substituted with one or more groups selected from a halogen atom, a cyano group, an amino group which may be protected, a hydroxyl group which may be protected, an aryl group which may be substituted with one or more groups selected from Substituent Group A and a heterocyclic group which may be substituted with one or more groups selected from Substituent Group A.

The $C_{1-6}$ alkyl group in the $C_{1-6}$ alkyl group which may be substituted of $R^3$ is preferably a $C_{1-3}$ alkyl group, and more preferably a methyl group.

m is an integer of 1 to 3, preferably an integer of 1 or 2, and more preferably an integer of 1.

m number of $R^4$'s are the same or different and are a hydrogen atom or a $C_{1-6}$ alkyl group which may be substituted, and preferably a hydrogen atom.

Even in a case where other substituents are of any kind, the $C_{1-6}$ alkyl group of $R^4$ may be substituted with one or more groups selected from a halogen atom, a cyano group, an amino group which may be protected and a hydroxyl group which may be protected.

One $R^4$ selected from m number of $R^4$'s together with $R^3$ may form a $C_{1-6}$ alkylene group which may be substituted, and the $C_{1-6}$ alkylene group in the $C_{1-6}$ alkylene group which may be substituted is preferably a $C_{1-3}$ alkylene group and more preferably a propylene group. The substituent of the $C_{1-6}$ alkylene group which may be substituted is preferably a halogen atom, a hydroxyl group or a $C_{1-3}$ alkoxy group, more preferably a fluorine atom, a hydroxyl group or a methoxy group, and more preferably a fluorine atom or a methoxy group.

m number of $R^5$'s are the same or different and are a hydrogen atom or a $C_{1-6}$ alkyl group which may be substituted, a $C_{2-6}$ alkenyl group which may be substituted or a $C_{2-6}$ alkynyl group which may be substituted, and preferably a $C_{1-6}$ alkyl group which may be substituted.

Even in a case where other substituents are of any kind, the $C_{1-6}$ alkyl group which may be substituted, $C_{2-6}$ alkenyl group which may be substituted or $C_{2-6}$ alkynyl group which may be substituted, of $R^5$, may be substituted with one or more groups selected from a halogen atom, a cyano group, an amino group which may be protected and a hydroxyl group which may be protected.

The $C_{1-6}$ alkyl group in the $C_{1-6}$ alkyl group which may be substituted of $R^5$ is preferably a $C_{1-3}$ alkyl group, and more preferably a methyl group.

n is an integer of 0 to 3, preferably an integer of 0 or 1, and more preferably an integer of 0.

n number of $R^6$'s are the same or different and are a hydrogen atom or a $C_{1-6}$ alkyl group which may be substituted, preferably a hydrogen atom or a $C_{1-6}$ alkyl group, and more preferably a hydrogen atom.

n number of $R^7$'s are the same or different and are a hydrogen atom or a $C_{1-6}$ alkyl group which may be substituted, preferably a hydrogen atom or a $C_{1-6}$ alkyl group, and more preferably a hydrogen atom.

Even in a case where other substituents are of any kind, the $C_{1-6}$ alkyl group of $R^6$ and $R^7$ may be substituted with a halogen atom, a cyano group, an amino group which may be protected or a hydroxyl group which may be protected.

$R^8$ is a hydrogen atom, a $C_{1-6}$ alkyl group which may be substituted, a $C_{2-6}$ alkenyl group which may be substituted or a $C_{2-6}$ alkynyl group which may be substituted, and preferably a hydrogen atom.

Even in a case where other substituents are of any kind, the $C_{1-6}$ alkyl group, $C_{2-6}$ alkenyl group or $C_{2-6}$ alkynyl group of $R^8$ may be substituted with one or more groups selected from a halogen atom, a cyano group, an amino group which may be protected and a hydroxyl group which may be protected.

$R^9$ is a $C_{1-6}$ alkyl group which may be substituted, a $C_{2-6}$ alkenyl group which may be substituted or a $C_{2-6}$ alkynyl group which may be substituted or a $C_{3-8}$ cycloalkyl group which may be substituted, preferably a $C_{1-6}$ alkyl group which may be substituted or a $C_{3-8}$ cycloalkyl group which may be substituted, and more preferably a $C_{1-6}$ alkyl group which may be substituted.

Even in a case where other substituents are of any kind, the $C_{1-6}$ alkyl group, $C_{2-6}$ alkenyl group, $C_{2-6}$ alkynyl group or $C_{3-8}$ cycloalkyl group of $R^9$ may be substituted with one or more groups selected from a halogen atom, a cyano group, an amino group which may be protected, a hydroxyl group which may be protected and a $C_{1-6}$ alkoxy group which may be substituted with one or more groups selected from Substituent Group A.

The $C_{1-6}$ alkyl group which may be substituted of $R^9$ is preferably a $C_{1-6}$ alkyl group having no substituent.

The $C_{1-6}$ alkyl group in the $C_{1-6}$ alkyl group which may be substituted of $R^9$ is preferably a $C_{1-3}$ alkyl group.

The substituent of the $C_{1-6}$ alkyl group which may be substituted of $R^9$ is preferably a halogen atom or a $C_{1-3}$ alkoxy group, and more preferably a methoxy group.

$R^8$ and $R^9$, together with the nitrogen atom to which they are bonded, may form a cyclic amino group which may be substituted, and the cyclic amino group in the cyclic amino group which may be substituted is preferably a morpholinyl group.

Even in a case where other substituents are of any kind, the cyclic amino group which is formed by $R^8$ and $R^9$ together with the nitrogen atom to which they are bonded may be substituted with one or more groups selected from a halogen atom, a cyano group, an amino group which may be protected, a hydroxyl group which may be protected and an oxo group.

$R^{10}$ is a hydrogen atom, a $C_{1-6}$ alkyl group which may be substituted, a $C_{2-6}$ alkenyl group which may be substituted or a $C_{2-6}$ alkynyl group which may be substituted, and preferably a hydrogen atom.

Even in a case where other substituents are of any kind, the $C_{1-6}$ alkyl group, $C_{2-6}$ alkenyl group or $C_{2-6}$ alkynyl group of $R^{10}$ may be substituted with one or more groups selected from a halogen atom, a cyano group, an amino group which may be protected, a hydroxyl group which may be protected and a $C_{1-6}$ alkoxy group which may be substituted with one or more groups selected from Substituent Group A.

$R^{11}$ is a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted or a heterocyclic group which may be substituted, preferably a $C_{1-6}$ alkyl group which may be substituted, an aryl group which may be substituted or a heterocyclic group which may be substituted, and more preferably an aryl group which may be substituted or a heterocyclic group which may be substituted.

Even in a case where other substituents are of any kind, the $C_{1-6}$ alkyl group, $C_{2-6}$ alkenyl group, $C_{2-6}$ alkynyl group, $C_{3-8}$ cycloalkyl group, aryl group or heterocyclic group of $R^{11}$ may be substituted with one or more groups selected from a halogen atom, a cyano group, an amino group which may be protected, a hydroxyl group which may be protected and a $C_{1-6}$ alkoxy group which may be substituted with one or more groups selected from Substituent Group A.

The substituent of each of the $C_{1-6}$ alkyl group which may be substituted, $C_{3-8}$ cycloalkyl group which may be substituted, aryl group which may be substituted or heterocyclic group which may be substituted, of $R^{11}$, is preferably a $C_{1-6}$ alkoxy group which may be substituted with one or more groups selected from Substituent Group A-2.

Substituent Group A-2: a halogen atom, a $C_{1-6}$ alkyl group, a $C_{3-8}$ cycloalkyl group, a $C_{1-6}$ alkoxy group, and a heterocyclic group.

The $C_{1-6}$ alkyl group which may be substituted of $R^{11}$ is preferably a $C_{1-6}$ alkyl group which is substituted, more preferably a $C_{1-3}$ alkyl group which is substituted, and still more preferably an ethyl group which is substituted.

In a case where $R^{11}$ is a $C_{1-6}$ alkyl group which is substituted, the substituent of $C_{1-6}$ alkyl group is preferably a heterocyclic group, and more preferably a pyridyl group, a pyrrolidinyl group or a morpholinyl group.

The aryl group which may be substituted of $R^{11}$ is preferably an aryl group which is substituted, and more preferably a phenyl group which is substituted.

In a case where $R^{11}$ is a phenyl group which is substituted, the substituent of the phenyl group is preferably a halogen atom, a cyano group or a carbamoyl group, and more preferably a fluorine atom, a cyano group or a carbamoyl group.

In a case where $R^{11}$ is a phenyl group which is substituted, the phenyl group has no substituent at the o-position, preferably has a substituent at the m-position or p-position, and more preferably has a substituent only at the p-position.

Preferred substituents of the m-position or p-position are as described above.

The heterocyclic group which may be substituted of $R^{11}$ is preferably a pyridyl group which may be substituted, an indazolyl group which may be substituted, a pyrazolopyridinyl group which may be substituted or an isoquinolyl group which may be substituted.

In a case where $R^{11}$ is a pyridyl group which may be substituted, it is preferably a pyridyl group represented by the following Formula [I]:

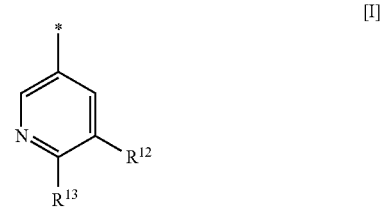

[I]

(in the formula, $R^{12}$ and $R^{13}$ are the same or different and represent a hydrogen atom, a halogen atom, a $C_{1-6}$ alkyl group, a $C_{1-6}$ alkoxy group, a $C_{1-6}$ alkylamino group or a heterocyclic group, and * represents a bonding position).

$R^{12}$ is a hydrogen atom, a halogen atom, a $C_{1-6}$ alkyl group, a $C_{1-6}$ alkoxy group, a $C_{1-6}$ alkylamino group or a heterocyclic group, and preferably a hydrogen atom.

$R^{13}$ is a hydrogen atom, a halogen atom, a $C_{1-6}$ alkyl group, a $C_{1-6}$ alkoxy group, a $C_{1-6}$ alkylamino group or a heterocyclic group, and preferably a halogen atom or a $C_{1-6}$ alkoxy group, and more preferably a fluorine atom or a methoxy group.

In a case where $R^{11}$ is an indazolyl group which may be substituted, it is preferably an indazolyl group represented by the following Formula [II]-(1) or [II]-(2):

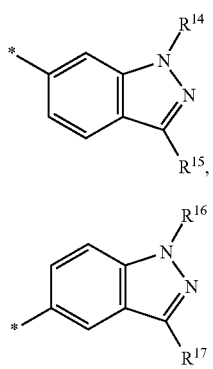

[II]-(1)

[II]-(2)

(in the formula, $R^{14}$ and $R^{16}$ are the same or different and represent a hydrogen atom or a $C_{1-6}$ alkyl group, $R^{15}$ and $R^{17}$ are the same or different and represent a hydrogen atom or a $C_{1-6}$ alkoxy group, and * represents a bonding position).

$R^{14}$ and $R^{16}$ are the same or different and are a hydrogen atom or a $C_{1-6}$ alkyl group, and preferably a hydrogen atom.

The $C_{1-6}$ alkyl group of $R^{14}$ and $R^{16}$ is preferably a $C_{1-3}$ alkyl group, and more preferably a methyl group.

$R^{15}$ and $R^{17}$ are the same or different and are a hydrogen atom or a $C_{1-6}$ alkoxy group, and preferably a hydrogen atom or a methoxy group.

The $C_{1-6}$ alkoxy group of $R^{15}$ and $R^{17}$ is preferably a methoxy group, an ethoxy group or a propoxy group, and more preferably a methoxy group.

In a case where $R^{11}$ is a pyrazolopyridinyl group which may be substituted, it is preferably a pyrazolopyridinyl group represented by the following Formula [III]:

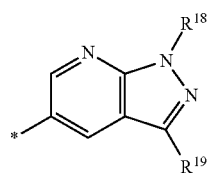

[III]

(in the formula, $R^{18}$ represents a hydrogen atom or a $C_{1-6}$ alkyl group which may be substituted with a $C_{1-6}$ alkoxy group, $R^{19}$ represents a hydrogen atom, a $C_{1-6}$ alkyl group which may be substituted with a $C_{1-6}$ alkoxy group or a $C_{1-6}$ alkoxy group, and * represents a bonding position).

$R^{18}$ is a hydrogen atom or a $C_{1-6}$ alkyl group which may be substituted with a $C_{1-6}$ alkoxy group, preferably a hydrogen atom or a $C_{1-3}$ alkyl group which may be substituted with a $C_{1-3}$ alkoxy group, more preferably a hydrogen atom, a methyl group, an ethyl group substituted with a methoxy group, and still more preferably a hydrogen atom or a methyl group.

$R^{19}$ is a hydrogen atom, a $C_{1-6}$ alkyl group which may be substituted with a $C_{1-6}$ alkoxy group or a $C_{1-6}$ alkoxy group, preferably a hydrogen atom, a $C_{1-3}$ alkyl group or a $C_{1-3}$ alkoxy group, and more preferably a hydrogen atom, a methyl group or a methoxy group.

The $C_{1-6}$ alkoxy group in the $C_{1-6}$ alkyl group which may be substituted with a $C_{1-6}$ alkoxy group, of $R^{18}$ and $R^{19}$, is preferably a methoxy group.

The $C_{1-6}$ alkyl group in the $C_{1-6}$ alkyl group which may be substituted with a $C_{1-6}$ alkoxy group, of $R^{18}$ and $R^{19}$, is preferably a $C_{1-3}$ alkyl group, and more preferably a methyl group.

In a case where $R^{11}$ is an isoquinolyl group which may be substituted, it is preferably an isoquinolyl group represented by the following Formula [IV]:

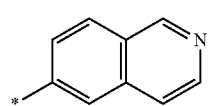

[IV]

(in the formula, * represents a bonding position).

$X^1$ is an oxygen atom, $N(R^{20})$ (in the formula, $R^{20}$ has the same meaning as defined above), $C(=O)$, $C(=O)$—$N(R^{20})$ (in the formula, $R^{20}$ has the same meaning as defined above) or a bond, and preferably $C(=O)$—$N(R^{20})$ (in the formula, $R^{20}$ has the same meaning as defined above).

$R^{20}$ is a hydrogen atom, a $C_{1-6}$ alkyl group which may be substituted, a $C_{2-6}$ alkenyl group which may be substituted or a $C_{2-6}$ alkynyl group which may be substituted, and preferably a hydrogen atom.

Even in a case where other substituents are of any kind, the $C_{1-6}$ alkyl group, $C_{2-6}$ alkenyl group or $C_{2-6}$ alkynyl group of $R^{20}$ may be substituted with one or more groups selected from a halogen atom, a cyano group, an amino group which may be protected and a hydroxyl group which may be protected.

$X^2$ is a $C_{1-6}$ alkylene group which may be substituted, a divalent alicyclic hydrocarbon group which may be substituted or a divalent aromatic hydrocarbon group which may be substituted, and preferably a $C_{1-6}$ alkylene group which may be substituted or a divalent alicyclic hydrocarbon group which may be substituted.

Even in a case where other substituents are of any kind, the $C_{1-6}$ alkylene group, divalent alicyclic hydrocarbon group or divalent aromatic hydrocarbon group of $X^2$ may be substituted with one or more groups selected from a halogen atom, a cyano group, an amino group which may be protected and a hydroxyl group which may be protected.

The $C_{1-6}$ alkylene group which may be substituted of $X^2$ is preferably a $C_{1-6}$ alkylene group which is unsubstituted.

The $C_{1-6}$ alkylene group in the $C_{1-6}$ alkylene group which may be substituted of $X^2$ is preferably a methylene group, an ethylene group or a trimethylene group, and more preferably a trimethylene group.

The substituent of the $C_{1-6}$ alkylene group which may be substituted of $X^2$ is preferably a $C_{1-6}$ alkyl group, more preferably a $C_{1-3}$ alkyl group, and still more preferably an ethyl group.

The divalent alicyclic hydrocarbon group which may be substituted of $X^2$ is preferably a divalent alicyclic hydrocarbon group which is unsubstituted.

The divalent alicyclic hydrocarbon group in the divalent alicyclic hydrocarbon group which may be substituted of $X^2$ is preferably a cyclobutylene group or a cyclohexylene group, and more preferably a cyclobutylene group.

In a case where $X^2$ is a cyclobutylene group, it is preferably a cyclobutylene group represented by the following Formula [2]:

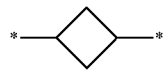

[2]

(in the formula, * represents a bonding position), and more preferably a cyclobutylene group represented by the following Formula [3]:

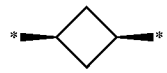

[3]

(in the formula, * represents a bonding position).

In a case where $X^2$ is a cyclohexylene group, it is preferably a cyclohexylene group represented by the following Formula [4]:

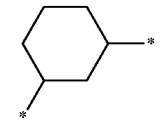

[4]

(in the formula, * represents a bonding position).

The divalent aromatic hydrocarbon group in the divalent aromatic hydrocarbon group which may be substituted of $X^2$ is preferably a phenylene group.

In a case where $X^2$ is a phenylene group, it is preferably a phenylene group represented by the following Formula [5]:

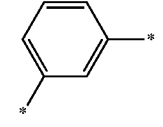

[5]

(in the formula, * is a bonding position).

The substituent of the divalent aromatic hydrocarbon group which may be substituted of $X^2$ is preferably a halogen atom or a $C_{1-6}$ alkyl group.

In a case where the substituent is a halogen atom, it is preferably a chlorine atom.

In a case where the substituent is a $C_{1-6}$ alkyl group, it is preferably a $C_{1-3}$ alkyl group, and more preferably a methyl group.

$X^3$ is a $C_{1-6}$ alkylene group which may be substituted, a $C_{2-6}$ alkenylene group which may be substituted, a $C_{2-6}$ alkynylene group which may be substituted or $N(R^{20})$—C(=O) (in the formula, $R^{20}$ has the same meaning as defined above), preferably a $C_{2-6}$ alkynylene group which may be substituted or $N(R^{20})$—C(=O) (in the formula, $R^{20}$ has the same meaning as defined above), and more preferably a $C_{2-6}$ alkynylene group which may be substituted.

Even in a case where other substituents are of any kind, the $C_{1-6}$ alkylene group, $C_{2-6}$ alkenylene group or $C_{2-6}$ alkynylene group of $X^3$ may be substituted with one or more groups selected from a halogen atom, a cyano group, an amino group which may be protected and a hydroxyl group which may be protected.

The $C_{2-6}$ alkynylene group in the $C_{2-6}$ alkynylene group which may be substituted of $X^3$ is preferably an ethynylene group.

Examples of salts of the compound of General Formula [1] include salts in basic groups such as amino groups, and salts in acidic groups such as a hydroxyl group and a carboxyl group, which are commonly known.

Examples of salts in basic groups include salts with mineral acids such as hydrochloric acid, hydrobromic acid, nitric acid and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid and trifluoroacetic acid; and salts with sulfonic acids such as methanesulfonic acid, benzenesulfonic acid, p-toluenesulfonic acid, mesitylene sulfonic acid and naphthalene sulfonic acid.

Examples of salts in acidic groups include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N'-dibenzylethylenediamine.

Among the salts mentioned above, preferred salts include pharmacologically acceptable salts.

The salt may be an anhydride, a hydrate or a solvate.

The compound represented by General Formula [1] or the salt thereof can be synthesized according to a known method, for example, the method described in WO2013/157540A described above.

[Novel Pharmaceutical Use of Compound of General Formula [1] and salt thereof]

The compound of General Formula [1] and the salt thereof are useful for the treatment of an FLT3 mutation-positive cancer.

<FLT3>

FLT3 is a polypeptide consisting of the amino acid sequence of SEQ ID NO: 1 (UniProt accession number: P36888), or a polypeptide substantially identical to the polypeptide consisting of the amino acid sequence of SEQ ID NO: 1. Further, FLT3 is a protein belonging to the class III of receptor tyrosine kinases, and activates the PI3K-AKT signaling pathway and ERK-MAPK signaling pathway to have an effect on cell growth, survival and differentiation. FLT3 is composed of five immnunoglobulin-like domains of an N-terminal extracellular domain, a transmembrane domain, a juxtamembrane domain, a tyrosine kinase domain (TKD) and a C-terminal domain.

According to the finding of the present inventors, the compound represented by General Formula [1] binds to FLT3 via a specific covalent bond with cysteine 695 of the amino acid sequence of SEQ ID NO: 1.

TKD is a polypeptide consisting of the amino acid sequence of amino acids 604 to 958 in the amino acid sequence of SEQ ID NO: 1, or a polypeptide substantially identical to the polypeptide consisting of the amino acid sequence of amino acids 604 to 958 in the amino acid sequence of SEQ ID NO: 1.

The gatekeeper domain of TKD is a polypeptide consisting of the amino acid sequence of amino acids 604 to 822 in the amino acid sequence of SEQ ID NO: 1, or a polypeptide substantially identical to the polypeptide consisting of the amino acid sequence of amino acids 604 to 822 in the amino acid sequence of SEQ ID NO: 1.

The mutation of the gatekeeper domain of TKD is known as one of causes of a resistance mechanism against kinase inhibitors. Among FLT3 inhibitors, there are those whose inhibitory effects on the FLT3 activity is markedly attenuated due to structural changes in the ATP-binding site, steric hindrance such as narrowing of the binding site or disappearance of the intermolecular interaction with amino acids at the mutation site being occurred by mutations of the gatekeeper domain.

The activation loop of TKD is a polypeptide consisting of the amino acid sequence of amino acids 823 to 861 in the amino acid sequence of SEQ ID NO: 1 or a polypeptide substantially identical to the polypeptide consisting of the amino acid sequence of amino acids 823 to 861 in the amino acid sequence of SEQ ID NO: 1.

The activation loop of TKD usually takes a folded structure between the N-terminal N lobe and C-terminal C lobe of TKD, and plays a role that prevents access of a substrate and ATP to the substrate-binding site and the ATP-binding site (FLT3 inactive form). On the other hand, when mutations occur in the amino acid located in the activation loop, in particular D835 or Y842, this leads to significant structural changes in the activation loop, whereby the ATP-binding site becomes an opened structure (FLT3 active form). Among FLT3 inhibitors that bind via an intermolecular interaction such as an electrostatic interaction or a hydrogen bond to the ATP-binding site of an FLT3 inactive form, there are also those whose FLT3 activity inhibitory activity is attenuated due to an intermolecular interaction with an FLT3 active form being incapable of being maintained and the binding force being lowered by a mutation of D835 or Y842.

The juxtamembrane domain of FLT3 is a polypeptide consisting of the amino acid sequence of amino acids 572 to 603 in the amino acid sequence of SEQ ID NO: 1, or a polypeptide substantially identical to the polypeptide consisting of the amino acid sequence of amino acids 572 to 603 in the amino acid sequence of SEQ ID NO: 1.

With respect to the juxtamembrane domain, it is known that mutations of amino acids with repeated amino acid sequences of various lengths may occur at various locations in such a domain.

The "substantially identical to a polypeptide" refers to having an amino acid sequence with deletion, substitution or addition of one or plural amino acids or having a high identity of an amino acid sequence (for example, having a sequence identity of 80% or more, preferably 90%, more preferably 95% or more, and still more preferably 98% or more), and also having the same function.

With respect to the amino acid sequence, unless otherwise stated, the "identity" refers to a percentage in consideration of the number of matched amino acids shared between two sequences, in a case where two sequences are aligned in an optimal manner. Search and analysis for the identity between amino acid sequences can be carried out by an algorithm or program (for example, BLASTP or ClustalW) well known to those skilled in the art. Parameters in the case of using the program can be appropriately set by those skilled in the art, and default parameters of each program may also be used. Specific procedures for such analytical methods are also well known to those skilled in the art.

<FLT3 Mutation>

The FLT3 mutation refers to that there is a mutation of an amino acid in the amino acid sequence of FLT3. In addition to the PI3K-AKT signaling pathway and ERK-MAPK signaling pathway, the STATS signaling pathway or other pathways may be activated by the mutation.

The mutation of an amino acid refers to deletion, substitution or addition of one or plural amino acids in an amino acid sequence. The mutation of amino acids include a case where any one of deletion, substitution or addition (for example, substitution) occurs in singular or plural number and a case where two or more selected from deletion, substitution and addition independently occur in combination of one or more thereof (for example, one substitution and three additions).

Additionally, the number and position of amino acids to be deleted, substituted or added in "deletion, substitution or addition of one or more amino acids" are not particularly limited as long as the resulting mutant has an intended function in any case. The number of amino acids to be deleted, substituted or added is, for example, 1 to 30, in any case.

The deletion of amino acid refers to a mutation where one or more amino acid residues in an amino acid sequence are deleted. The deletion includes a deletion of an amino acid residue from the end of an amino acid sequence and a deletion of an amino acid residue in the midway of an amino acid sequence.

The substitution of an amino acid refers to a mutation where one or more amino acid residues in an amino acid sequence are changed to one or more different amino acid residues.

The addition of an amino acid refers to a mutation where one or more amino acid residues are added in an amino acid sequence. The addition includes an addition of an amino acid residue to the end of an amino acid sequence and an addition of an amino acid residue in the midway of an amino acid sequence.

The FLT3 mutation preferably includes a TKD mutation. The TKD mutation encompasses a mutation in the gatekeeper domain of TKD and a mutation in the activation loop of TKD. The FLT3 mutation may also include an ITD mutation, in addition to a TKD mutation.

The TKD mutation refers to that there is a mutation in the amino acid sequence of TKD.

The mutation in the gatekeeper domain of TKD is, for example, mutation(s) of one or plural amino acids in the amino acids 604 to 822 region of the amino acid sequence of SEQ ID NO: 1, and preferably a mutation of at least one amino acid selected from the group consisting of amino acids 621, 627, 676, 691 and 697 in SEQ ID NO: 1. The mutation in the gatekeeper domain of TKD is more preferably a mutation of amino acid 691 in the amino acid sequence of SEQ ID NO: 1, and still more preferably a substitution of phenylalanine at amino acid 691 of SEQ ID NO: 1 to leucine. In any case, the resulting mutant of FLT3 has an FLT3 activity, and preferably a mutant FLT3 activity.

The mutation in the gatekeeper domain of TKD may also be made of any one of the following amino acid sequences. In any case, the resulting mutant of FLT3 has an FLT3 activity:

a. an amino acid sequence having a deletion, substitution or addition of phenylalanine 691 (preferably a substitution of phenylalanine 691, more preferably a substitution of phenylalanine 691 to leucine) in the amino acid sequence of SEQ ID NO: 1;

b. an amino acid sequence having a deletion, substitution or addition of one or plural amino acids other than amino acid 691 in the amino acid sequence of the above a; and c. an amino acid sequence having a 80% sequence identity to the amino acid sequence of the above a (provided that phenylalanine 691 has been deleted, substituted or added (preferably substituted, and more preferably substituted to leucine)).

The mutation in the activation loop of TKD is, for example, mutation(s) of one or plural amino acids in the amino acids 823 to 861 region of the amino acid sequence of SEQ ID NO: 1. Preferred is a mutation of at least one amino acid selected from the group consisting of amino acids 835, 836 and 842 in the amino acid sequence of SEQ ID NO: 1. More preferred is at least one mutation selected from the group consisting of the following:

a. a substitution of aspartic acid 835 in the amino acid sequence of SEQ ID NO: 1 to valine, tyrosine, histidine, glutamic acid or asparagine;

b. a substitution of isoleucine 836 in the amino acid sequence of SEQ ID NO: 1 to leucine-aspartic acid; and c. a substitution of tyrosine 842 in the amino acid sequence of SEQ ID NO: 1 to cysteine or histidine.

In any case, the resulting mutant of FLT3 has an FLT3 activity, and preferably a mutant FLT3 activity.

The mutation in the activation loop of TKD may also be made of any one of the following amino acid sequences. In any case, the resulting mutant of FLT3 has an FLT3 activity:

a. an amino acid sequence having a deletion, substitution or addition of aspartic acid 835 (preferably a substitution of aspartic acid 835, and more preferably a substitution of aspartic acid 835 to valine, tyrosine, histidine, glutamic acid or asparagine) in the amino acid sequence of SEQ ID NO: 1;

b. an amino acid sequence having a deletion, substitution or addition of one or plural amino acids other than amino acid 835 in the amino acid sequence of the above a;

c. an amino acid sequence having a 80% sequence identity to the amino acid sequence of the above a (provided that aspartic acid 835 has been deleted, substituted or added (preferably substituted, and more preferably substituted to valine, tyrosine, histidine, glutamic acid or asparagine));

d. an amino acid sequence having a deletion, substitution or addition of isoleucine 836 (preferably a substitution or deletion of isoleucine 836, and more preferably a substitution of isoleucine 836 to leucine-asparagine) in the amino acid sequence of SEQ ID NO: 1;

e. an amino acid sequence having a deletion, substitution or addition of one or plural amino acids other than amino acid 836 in the amino acid sequence of the above d;

f. an amino acid sequence having a 80% sequence identity to the amino acid sequence of the above d (provided that isoleucine 836 has been deleted, substituted or added (preferably substituted or deleted, and more preferably substituted to leucine-asparagine));

g. an amino acid sequence having a deletion, substitution or addition of tyrosine 842 (preferably a substitution of tyrosine 842, and more preferably a substitution of tyrosine 842 to cysteine or histidine) in the amino acid sequence of SEQ ID NO: 1;

h. an amino acid sequence having a deletion, substitution or addition of one or plural amino acids other than amino acid 842 in the amino acid sequence of the above g;

i. an amino acid sequence having a 80% sequence identity to the amino acid sequence of the above g (provided that tyrosine 842 has been deleted, substituted or added (preferably substituted, and more preferably substituted to cysteine or histidine)).

Whether or not the resulting mutant of FLT3 has an FLT3 activity or whether or not the resulting mutant of FLT3 has a mutant FLT3 activity can be measured and determined by those skilled in the art according to a known method. With respect to a more specific measuring method and judgmental standards, a reference may be made to the description of the Examples section of the above-mentioned WO2013/157540A and the description of the Examples section of the present specification. Additionally, whether or not the resulting mutant of FLT3 has a mutant FLT3 activity can be determined based on a reference that the resulting mutant of FLT3 has an FLT3 activity but it is not inhibited by an FLT3 inhibitor of the related art, preferably at least one FLT3 inhibitor selected from the group consisting of Quizartinib (Ambit Biosciences Corporation) and Sorafenib (Bayer HealthCare Pharmaceuticals, Inc.). With respect to the phrase "is not inhibited", it can be determined, for example, using the measuring method described in the Examples section of the present specification and with reference to the judgmental standards including an $IC_{50}$ value of 10 nmol/L or 100 nmol/L or more in an enzyme inhibition assay, a $GI_{50}$ value of 10 nmol/L or 100 nmol/L or more in a cell growth assay, and an $IC_{50}$ value of 90 nmol/L or more in an intracellular phosphorylation inhibition assay.

The ITD mutation refers to a mutation where the amino acid sequence in the juxtamembrane domain of FLT3 is repeated at various sites within such a domain The repeating length of the amino acid sequence in the ITD mutation has been reported to vary from 2 to 42 amino acids. In particular, in many cases with the ITD mutation, such a mutation is observed with a high frequency in the amino acid sequence of amino acids 591 to 599 of SEQ ID NO: 1. For an ITD mutation and FLT3 having an ITD mutation, a reference may be made to WO2000/011470A (JP4542268B).

<FLT3 Mutation-Positive>

The expression that a certain cancer is FLT3 mutation-positive refers to that there is a mutation in the amino acid sequence of FLT3 in the cancer cells. In addition, the "FLT3 mutation-positive" also refers to that there is a mutation in the FLT3 gene so as to encode an amino acid sequence having such a mutation. In a case where there is a mutation in the amino acid sequence of FLT3, it is clear that there is a mutation in the FLT3 gene.

Whether or not it is FLT3 mutation-positive, that is, mutations of FLT3 can be investigated by analyzing the gene sequence of FLT3 or the sequence of mRNA which is a transcription product of FLT3. The analysis method of sequences may be, for example, a dideoxynucleotide chain termination method (Sanger et al., (1977) Proc. Natal. Acad. Sci. USA 74:5463). It is also possible to analyze sequences by using an appropriate DNA sequencer.

Further, mutations of FLT3 may also be analyzed by a method such as in situ hybridization, Southern blot analysis, Northern blot analysis, DNA microarray, Reverse Transcription Polymerase Chain Reaction (RT-PCR), Fragment analysis, PCR-Single-Strand Conformation Polymorphism-PCR (PCR-SSCP), PCR-Restriction fragment length polymorphism (PCR-RFLP), amplification refractory mutation system (ARMS), peptide nucleic acid (PNA)-LNA PCR clamp, PCR-Invader, Scorpion ARMS, Cyleave, iPLEX or SMart Amplification Process (SMAP). These methods can be used according to a conventional method.

Examples of a specimen for the detection of mutations of FLT3 include blood, bone marrow, surgical specimen and biopsy specimen.

A compound of General Formula [1] and a salt thereof can be used in a variety of cancers. The expression of FLT3 is limited to early progenitor cells, but in blood cancer, FLT3 is expressed at high levels or FLT3 undergoes gene mutation, thereby contributing to malignant growth of cancer through the activation of the signaling pathways. Examples of the blood cancer for which the compound of General Formula [1] and the salt thereof is effective include acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large cell lymphoma (ALCL), prolymphocytic leukemia (PML), juvenile myelomonocytic leukemia (JMML), adult T cell ALL, myelodysplastic syndrome (MDS) and myeloproliferative disease (MPD).

The compound of General Formula [1] and the salt thereof can be used for these cancers which are FLT3 mutation-positive.

[Dosage Form and Others]

A compound of General Formula [1] or a salt thereof can be used as an active ingredient of a mutant FLT3 inhibitor. Preferably, the compound of General Formula [1] or the salt thereof can be used as an agent which inhibits a mutant FLT3 containing a TKD mutation. Such an agent may also be one that inhibits a wild-type FLT3. The mutant FLT3 inhibitor containing the compound of General Formula [1] or the salt thereof as an active ingredient is particularly useful as an anticancer agent.

The pharmaceutical composition or agent may contain only one of or two or more of the compound of General Formula [1] and various salts thereof. The pharmaceutical composition of the present invention may be used in combination with other therapeutic agents including a known anti-tumor agent which has been conventionally used in the art.

Typically, additives such as an excipient, a binder, a lubricant, a disintegrating agent, a coloring agent, a flavoring agent, an emulsifier, a surfactant, a solubilizing agent, a suspending agent, a tonicity agent, a buffering agent, a preservative, an antioxidant, a stabilizer and an absorption accelerator, which have been used in the formulation, may be added to the pharmaceutical composition or agent.

Examples of the administration route of a pharmaceutical composition or agent include methods such as intravenous, intraarterial, rectal, intraperitoneal, intramuscular, intratumoral or intravesical injection method, oral administration, transdermal administration and suppositories. With respect to the dosage and frequency of administration, for example, for an adult, for example a dose of 0.01 to 1000 mg/kg/day can be administered once or in several divided portions by oral or parenteral administration (for example, injection, infusion or rectal administration). Examples of the dosage form include tablets, capsules, powders, syrups, granules, pills, suspensions, emulsions, solutions, powder preparations, suppositories, eye drops, nasal drops, ear drops, patches, ointments and injections.

As described so far, the compound of General Formula [1] or the salt thereof can be considered to be particularly effective for FLT3 mutation-positive cancers. Accordingly, an FLT3 gene assay for investigating the presence or absence of FLT3 mutations may be carried out in order to predict an effect of the treatment with a pharmaceutical composition or agent containing the compound of General Formula [1] or the salt thereof; in order to select a subject to whom a pharmaceutical composition is applied; and also in order to determine the applicability of the treatment with a pharmaceutical composition or agent. The present application also provides these embodiments.

With respect to FLT3 inhibitors of the related art, there may be some cases where the activity of an FLT3 inhibitor against FLT3 is high, but the effectiveness thereof is significantly poor for a certain mutant FLT3. Meanwhile, according to the study conducted by the present inventors, a compound of General Formula [1] or a salt thereof may be effective for a variety of mutant FLT3s. In particular, with respect to mutations in the activation loop and more specifically mutations in the amino acid 835, 836 or 842 of the amino acid sequence of SEQ ID NO: 1, the compound of General Formula [1] or the salt thereof may be effective against a variety of mutant FLT3s.

Hereinafter, the present invention will be described with reference to the following Examples, but the present invention is not limited thereto.

EXAMPLES

Preparation Example

Compounds described in Tables 1-1 to 1-4 were synthesized according to the method described in the above-mentioned WO2013/157540A.

TABLE 1-1

Structure

1

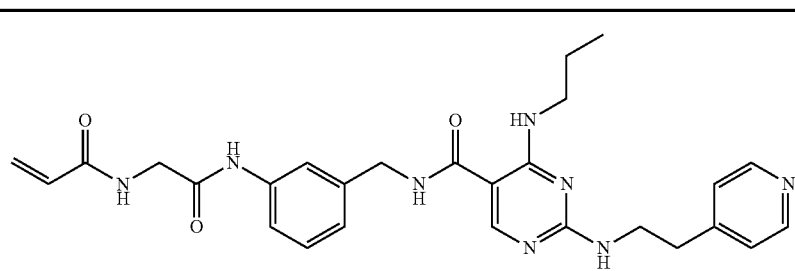

TABLE 1-1-continued

| | Structure |
|---|---|
| 2 | (chemical structure) |
| 3 | (chemical structure) |
| 4 | (chemical structure) |
| 5 | (chemical structure) |
| 6 | (chemical structure) |
| 7 | (chemical structure) |

TABLE 1-1-continued
Structure
8 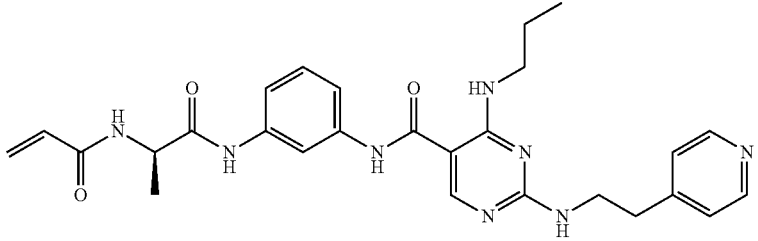 [SMILES: C=CC(=O)N[C@H](C)C(=O)Nc1cccc(NC(=O)c2cnc(NCCc3ccncc3)nc2NCCC)c1]
9 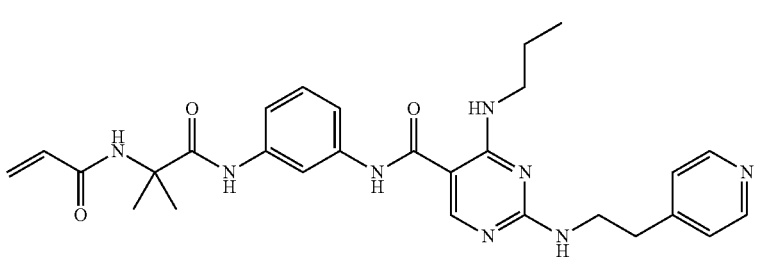 [SMILES: C=CC(=O)NC(C)(C)C(=O)Nc1cccc(NC(=O)c2cnc(NCCc3ccncc3)nc2NCCC)c1]
10 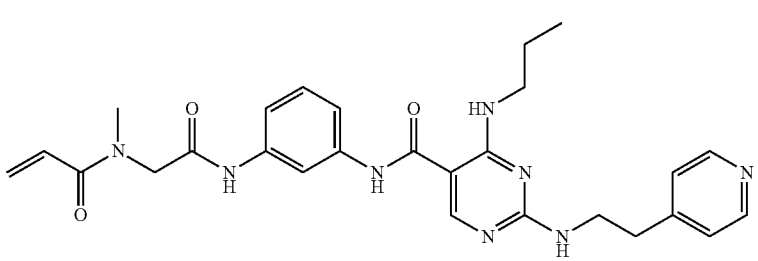 [SMILES: C=CC(=O)N(C)CC(=O)Nc1cccc(NC(=O)c2cnc(NCCc3ccncc3)nc2NCCC)c1]
11 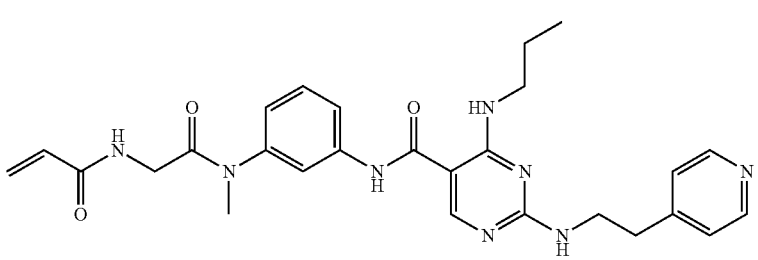 [SMILES: C=CC(=O)NCC(=O)N(C)c1cccc(NC(=O)c2cnc(NCCc3ccncc3)nc2NCCC)c1]
12 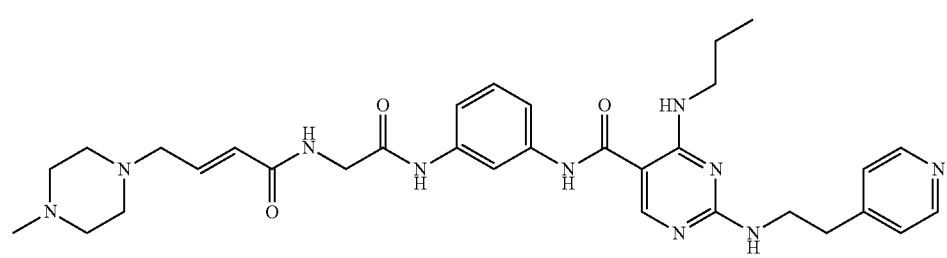 [SMILES: CCCNc1nc(NCCc2ccncc2)ncc1C(=O)Nc1cccc(NC(=O)CNC(=O)/C=C/CN2CCN(C)CC2)c1]
13 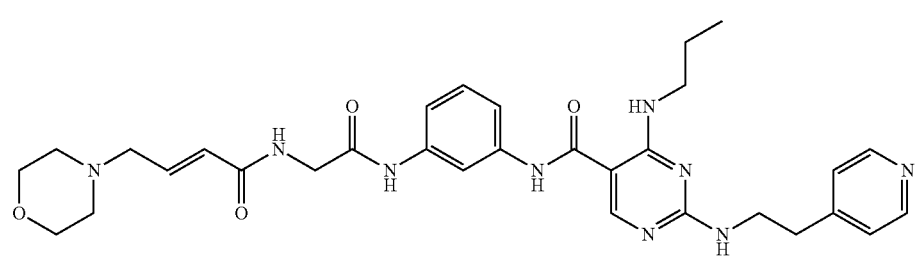 [SMILES: CCCNc1nc(NCCc2ccncc2)ncc1C(=O)Nc1cccc(NC(=O)CNC(=O)/C=C/CN2CCOCC2)c1]

TABLE 1-1-continued
Structure
14 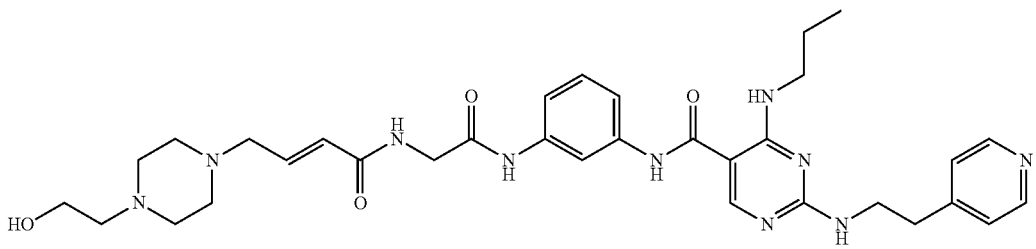 [SMILES: CCCNc1nc(NCCc2ccncc2)ncc1C(=O)Nc1cccc(NC(=O)CNC(=O)/C=C/CN2CCN(CCO)CC2)c1]
15 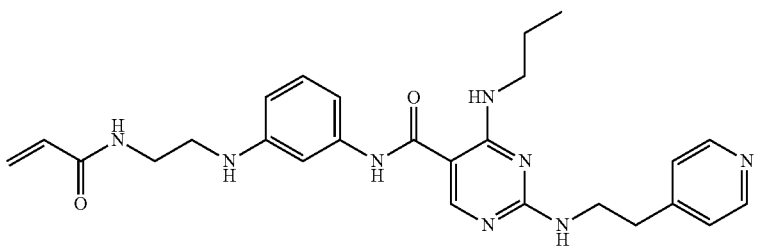 [SMILES: C=CC(=O)NCCNc1cccc(NC(=O)c2cnc(NCCc3ccncc3)nc2NCCC)c1]
16 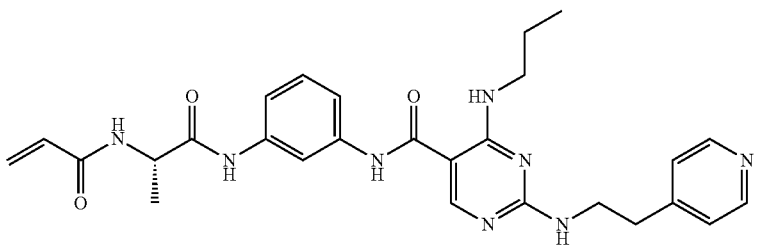 [SMILES: C=CC(=O)N[C@@H](C)C(=O)Nc1cccc(NC(=O)c2cnc(NCCc3ccncc3)nc2NCCC)c1]
17 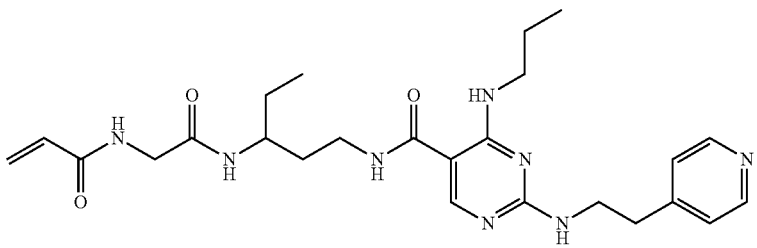 [SMILES: C=CC(=O)NCC(=O)NC(CC)CCNC(=O)c1cnc(NCCc2ccncc2)nc1NCCC]
18 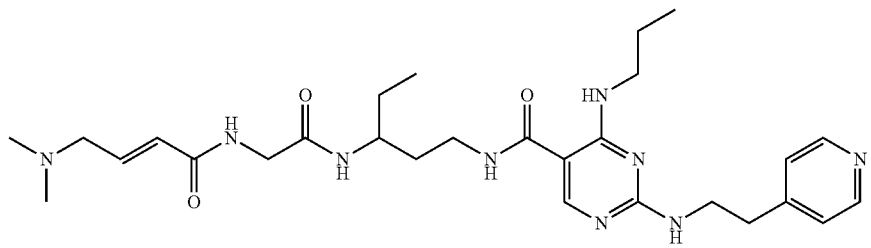
19 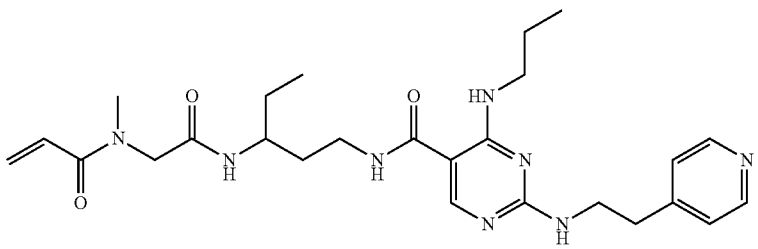 [SMILES: C=CC(=O)N(C)CC(=O)NC(CC)CCNC(=O)c1cnc(NCCc2ccncc2)nc1NCCC]

TABLE 1-1-continued

| | Structure |
|---|---|
| 20 | (chemical structure) |

TABLE 1-2

| | Structure |
|---|---|
| 21 | (chemical structure) |
| 22 | (chemical structure) |
| 23 | (chemical structure) |
| 24 | (chemical structure) |

TABLE 1-2-continued
| | Structure |
|---|---|
| 25 | 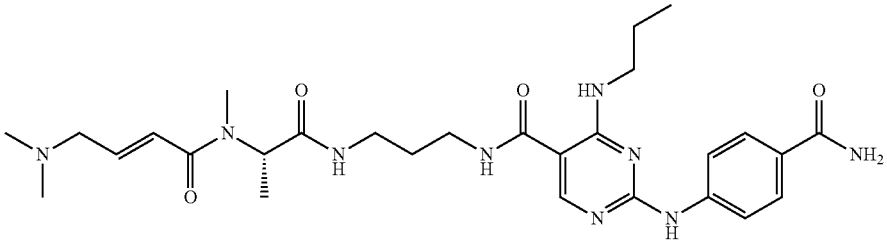 [SMILES: CCCNc1nc(Nc2ccc(C(N)=O)cc2)ncc1C(=O)NCCCNC(=O)[C@H](C)N(C)C(=O)/C=C/CN(C)C] |
| 26 | 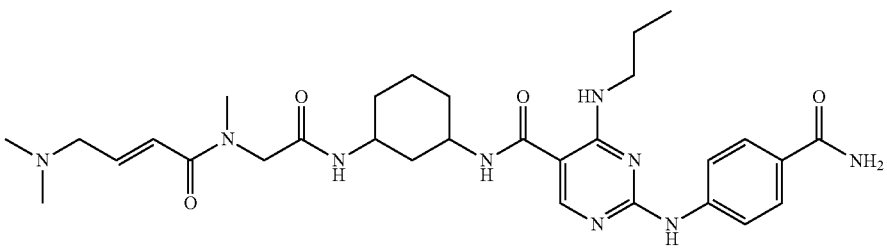 [SMILES: CCCNc1nc(Nc2ccc(C(N)=O)cc2)ncc1C(=O)NC1CCCC(NC(=O)CN(C)C(=O)/C=C/CN(C)C)C1] |
| 27 | 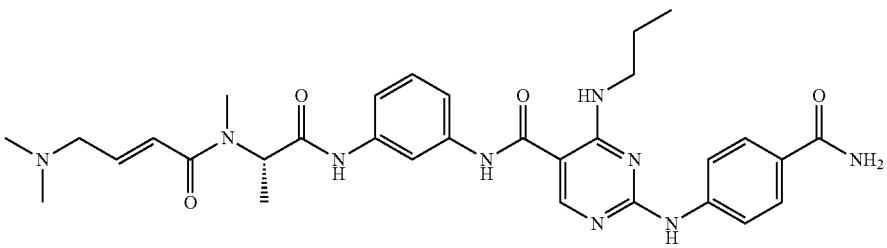 [SMILES: CCCNc1nc(Nc2ccc(C(N)=O)cc2)ncc1C(=O)Nc1cccc(NC(=O)[C@H](C)N(C)C(=O)/C=C/CN(C)C)c1] |
| 28 | 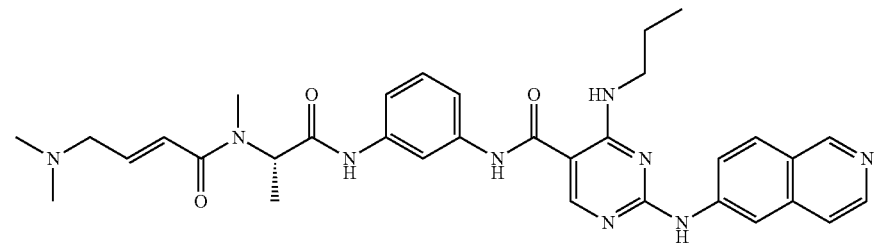 [SMILES: CCCNc1nc(Nc2ccc3cnccc3c2)ncc1C(=O)Nc1cccc(NC(=O)[C@H](C)N(C)C(=O)/C=C/CN(C)C)c1] |
| 29 | 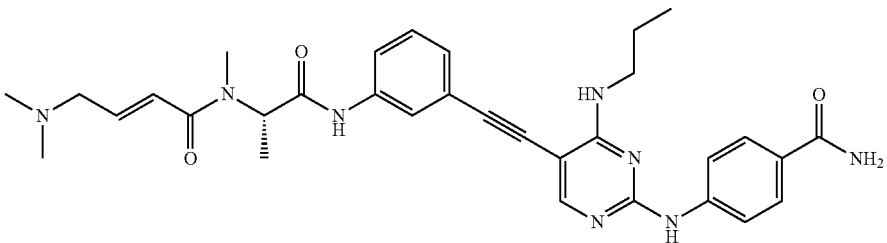 [SMILES: CCCNc1nc(Nc2ccc(C(N)=O)cc2)ncc1C#Cc1cccc(NC(=O)[C@H](C)N(C)C(=O)/C=C/CN(C)C)c1] |
| 30 | 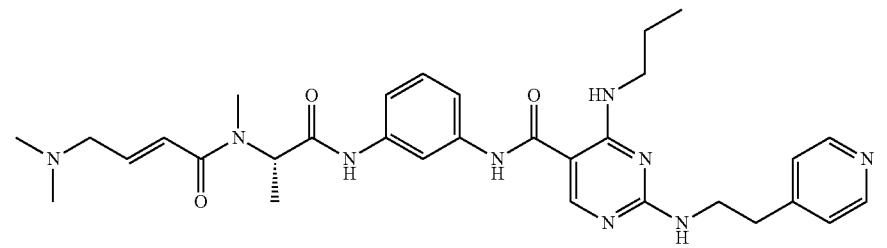 [SMILES: CCCNc1nc(NCCc2ccncc2)ncc1C(=O)Nc1cccc(NC(=O)[C@H](C)N(C)C(=O)/C=C/CN(C)C)c1] |

US 9,987,278 B2
TABLE 1-2-continued
Structure
31 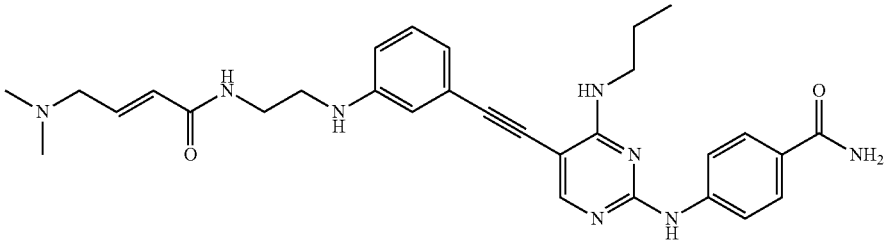 [SMILES: CCCNc1nc(Nc2ccc(C(N)=O)cc2)ncc1C#Cc1cccc(NCCNC(=O)/C=C/CN(C)C)c1]
32 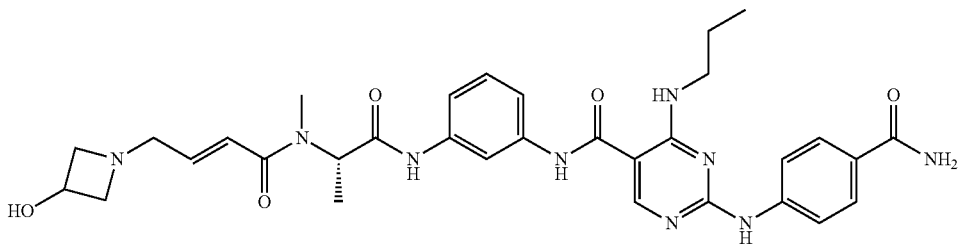 [SMILES: CCCNc1nc(Nc2ccc(C(N)=O)cc2)ncc1C(=O)Nc1cccc(NC(=O)[C@H](C)N(C)C(=O)/C=C/CN2CC(O)C2)c1]
33 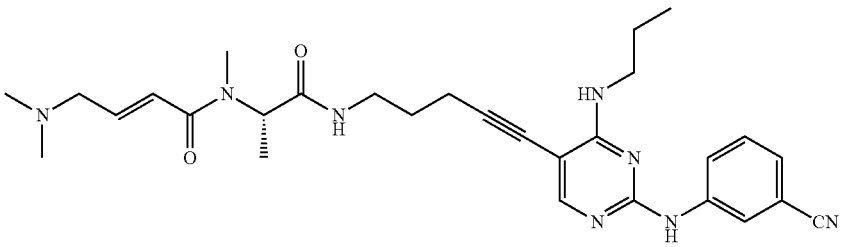 [SMILES: CCCNc1nc(Nc2cccc(C#N)c2)ncc1C#CCCCNC(=O)[C@H](C)N(C)C(=O)/C=C/CN(C)C]
34 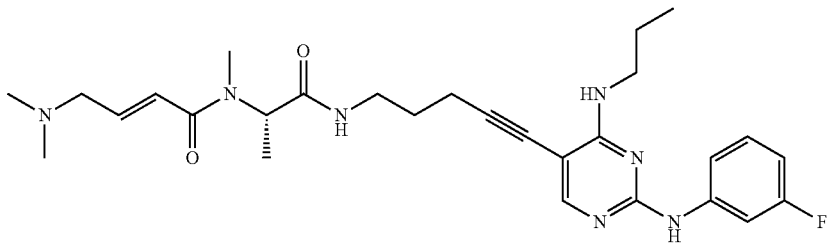 [SMILES: CCCNc1nc(Nc2cccc(F)c2)ncc1C#CCCCNC(=O)[C@H](C)N(C)C(=O)/C=C/CN(C)C]
35 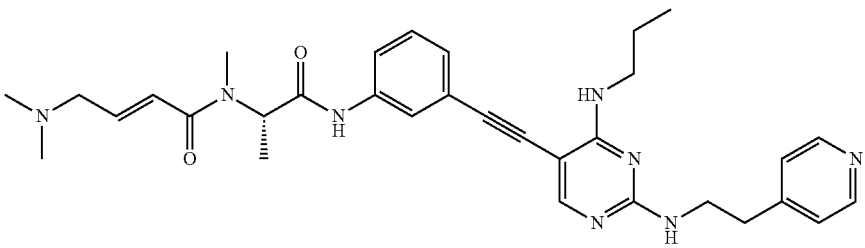 [SMILES: CCCNc1nc(NCCc2ccncc2)ncc1C#Cc1cccc(NC(=O)[C@H](C)N(C)C(=O)/C=C/CN(C)C)c1]
36 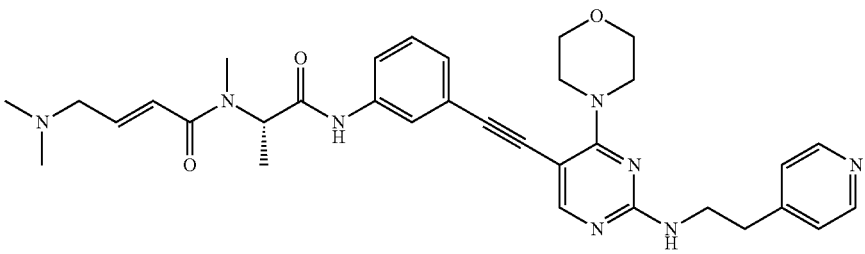 [SMILES: C[C@@H](C(=O)Nc1cccc(C#Cc2cnc(NCCc3ccncc3)nc2N2CCOCC2)c1)N(C)C(=O)/C=C/CN(C)C]

TABLE 1-2-continued

| | Structure |
|---|---|
| 37 | (chemical structure) |
| 38 | (chemical structure) |
| 39 | (chemical structure) |
| 40 | (chemical structure) |

TABLE 1-3

| | Structure |
|---|---|
| 41 | (chemical structure) |

TABLE 1-3-continued
Structure
42 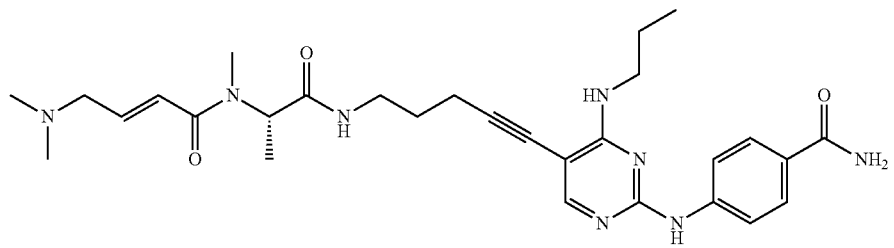 [SMILES: CCCNc1nc(Nc2ccc(C(N)=O)cc2)ncc1C#CCCCNC(=O)[C@H](C)N(C)C(=O)/C=C/CN(C)C]
43 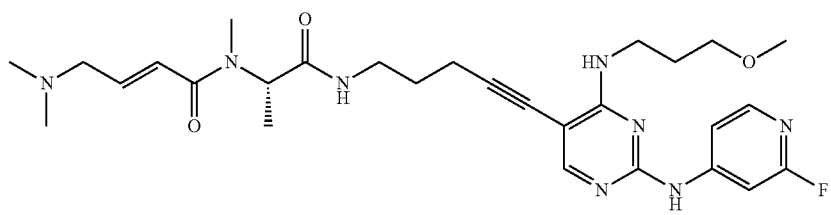 [SMILES: COCCCNc1nc(Nc2ccnc(F)c2)ncc1C#CCCCNC(=O)[C@H](C)N(C)C(=O)/C=C/CN(C)C]
44 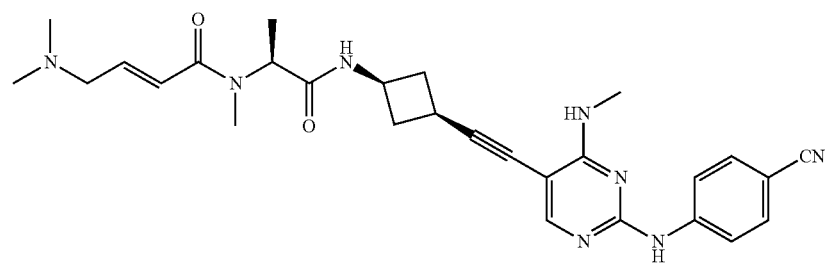 [SMILES: CNc1nc(Nc2ccc(C#N)cc2)ncc1C#C[C@H]1C[C@@H](NC(=O)[C@H](C)N(C)C(=O)/C=C/CN(C)C)C1]
45 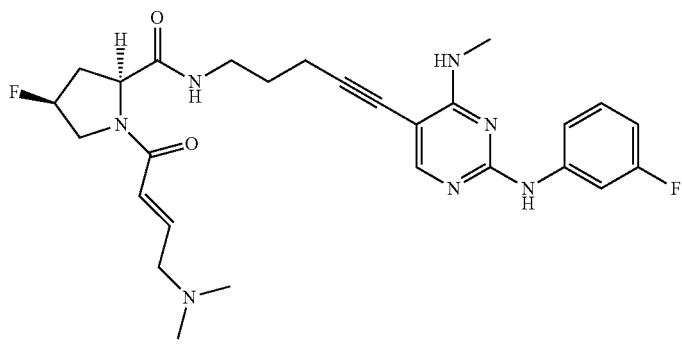 [SMILES: CNc1nc(Nc2cccc(F)c2)ncc1C#CCCCNC(=O)[C@@H]1C[C@H](F)CN1C(=O)/C=C/CN(C)C]
46 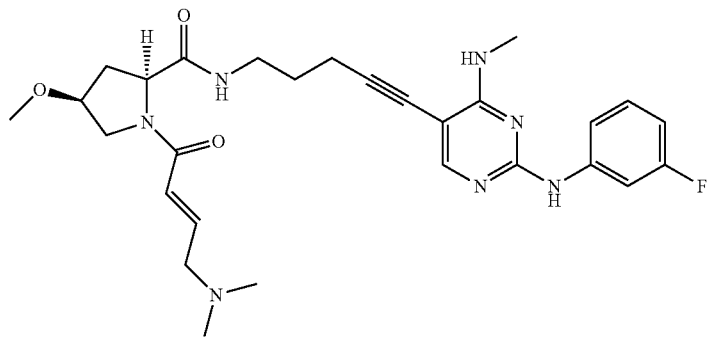 [SMILES: CNc1nc(Nc2cccc(F)c2)ncc1C#CCCCNC(=O)[C@@H]1C[C@H](OC)CN1C(=O)/C=C/CN(C)C]

TABLE 1-3-continued

Structure

47

48

49

50

51

52

TABLE 1-3-continued
Structure
53 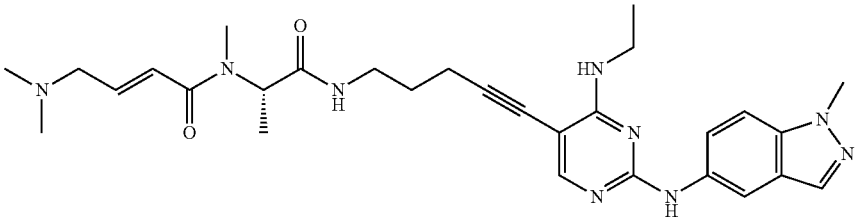 [SMILES: CCNc1nc(Nc2ccc3c(cnn3C)c2)ncc1C#CCCCNC(=O)[C@H](C)N(C)C(=O)/C=C/CN(C)C]
54 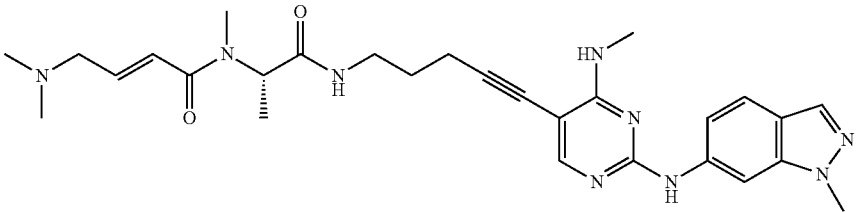 [SMILES: CNc1nc(Nc2ccc3cnn(C)c3c2)ncc1C#CCCCNC(=O)[C@H](C)N(C)C(=O)/C=C/CN(C)C]
55 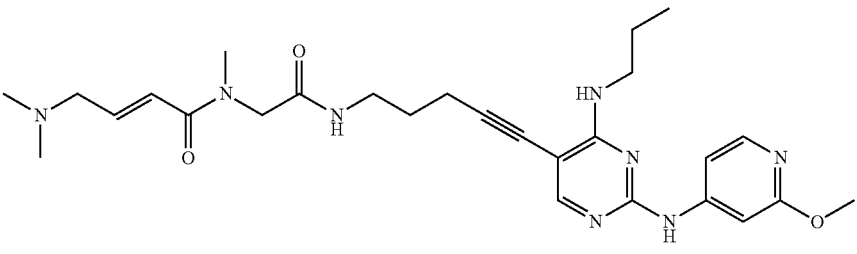
56 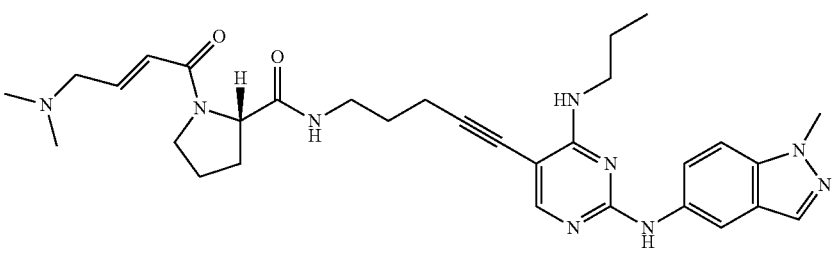 [SMILES: CCCNc1nc(Nc2ccc3c(cnn3C)c2)ncc1C#CCCCNC(=O)[C@@H]1CCCN1C(=O)/C=C/CN(C)C]
57 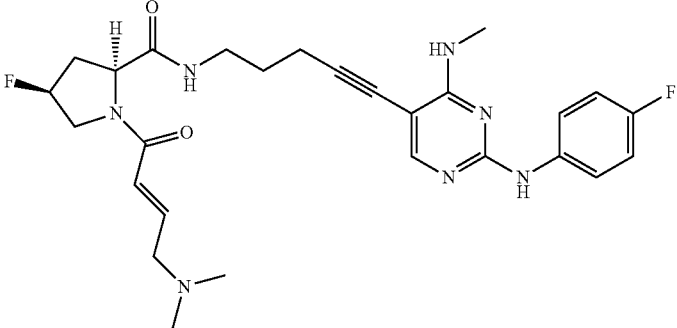 [SMILES: CNc1nc(Nc2ccc(F)cc2)ncc1C#CCCCNC(=O)[C@@H]1C[C@H](F)CN1C(=O)/C=C/CN(C)C]

TABLE 1-3-continued
| | Structure |
|---|---|
| 58 | 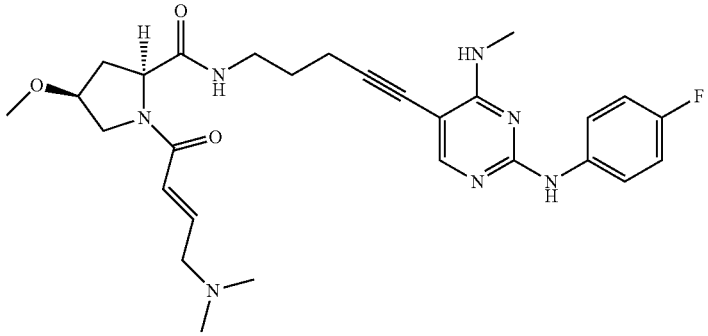 [SMILES: CNc1nc(Nc2ccc(F)cc2)ncc1C#CCCCNC(=O)[C@@H]1C[C@H](OC)CN1C(=O)/C=C/CN(C)C] |
| 59 | 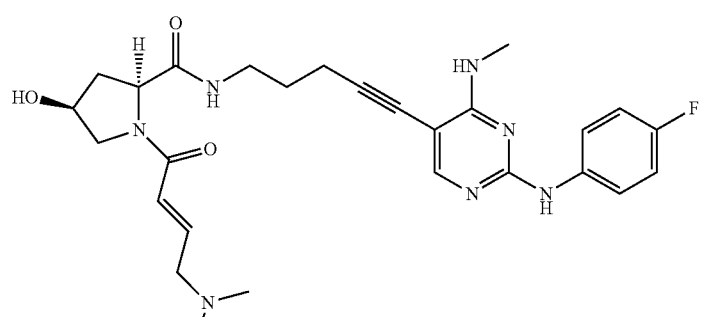 |
| 60 | 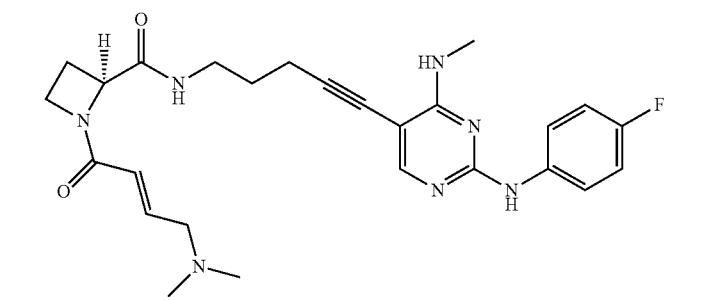 [SMILES: CNc1nc(Nc2ccc(F)cc2)ncc1C#CCCCNC(=O)[C@@H]1CCN1C(=O)/C=C/CN(C)C] |
TABLE 1-4
| | Structure |
|---|---|
| 61 | 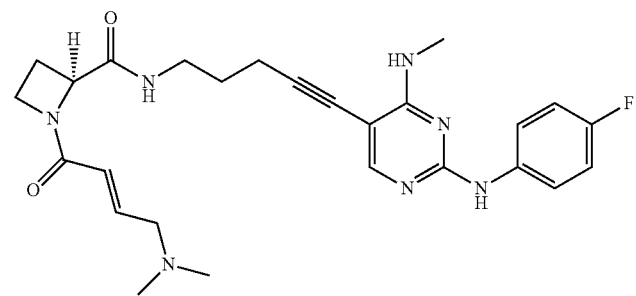 [SMILES: CNc1nc(Nc2ccc(F)cc2)ncc1C#CCCCNC(=O)[C@@H]1CCN1C(=O)/C=C/CN(C)C] |

TABLE 1-4-continued

| | Structure |
|---|---|
| 62 | 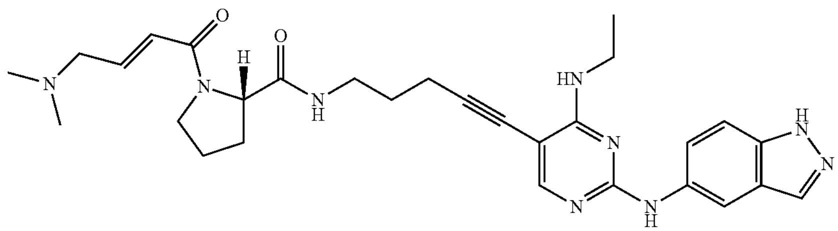 [SMILES: CCNc1nc(Nc2ccc3[nH]ncc3c2)ncc1C#CCCCNC(=O)[C@@H]1CCCN1C(=O)/C=C/CN(C)C] |
| 63 | 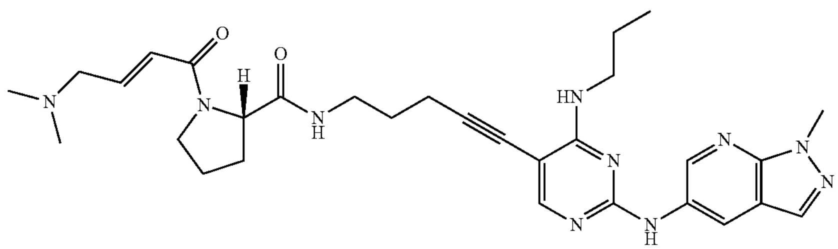 [SMILES: CCCNc1nc(Nc2cnc3c(cnn3C)c2)ncc1C#CCCCNC(=O)[C@@H]1CCCN1C(=O)/C=C/CN(C)C] |
| 64 | 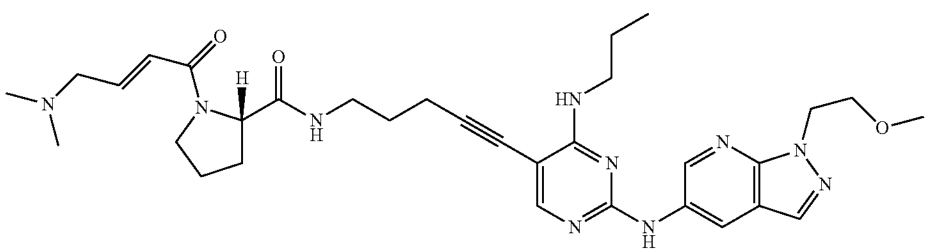 |
| 65 | 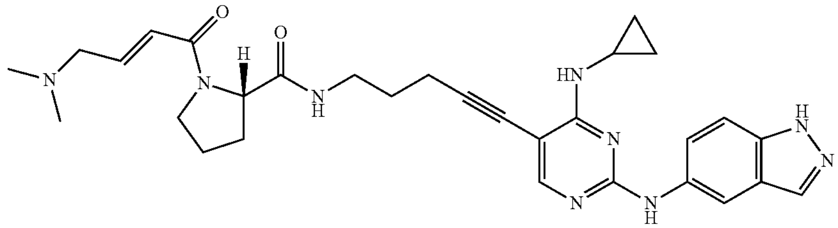 [SMILES: CN(C)C/C=C/C(=O)N1CCC[C@H]1C(=O)NCCCC#Cc1cnc(Nc2ccc3[nH]ncc3c2)nc1NC1CC1] |
| 66 | 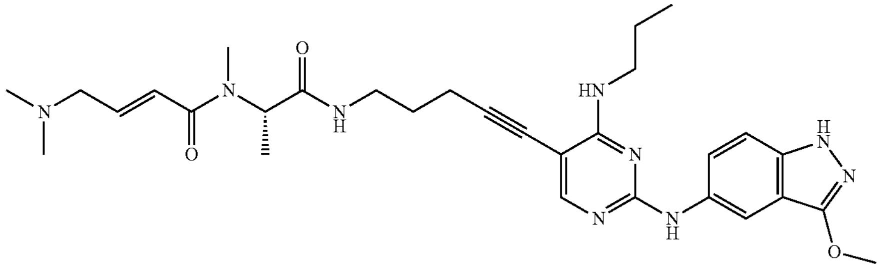 |
| 67 | 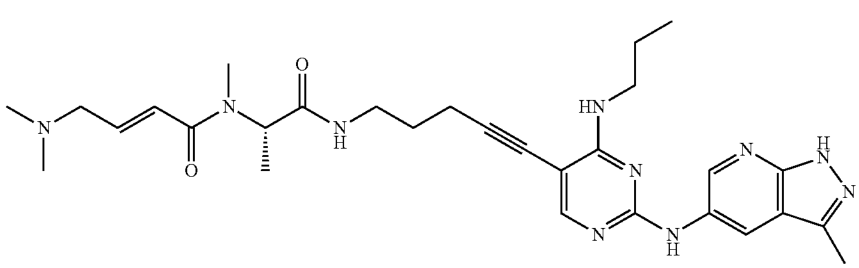 [SMILES: CCCNc1nc(Nc2cnc3[nH]nc(C)c3c2)ncc1C#CCCCNC(=O)[C@H](C)N(C)C(=O)/C=C/CN(C)C] |

TABLE 1-4-continued

| Structure |
|---|
| 68 (chemical structure) |
| 69 (chemical structure) |
| 70 (chemical structure) |
| 71 (chemical structure) |
| 72 (chemical structure) |

Example 1

Mutant FLT3 (FLT3 D835Y) Enzyme Inhibition Assay

Quizartinib (Ambit Biosciences Corporation) was used as Reference Compound 1.

6 μL (0.75 ng) of a mutant FLT3 protein (FLT3 D835Y, Life Technologies) and 3 μL of a solution (100 mmol/L HEPES, 10 mmol/L MgCl$_2$, 25 mmol/L NaCl, 0.01% BSA, 1 mmol/L DTT, pH 7.5) containing a predetermined concentration of a test compound were mixed and allowed to incubate at 25° C. for 15 minutes. Thereafter, 3 μL (final concentration: 0.25 μmol/L) of a substrate peptide Biotin-AAA-AEEEEYFELVAKKK (Toray Industries, Inc.) (SEQ ID NO: 2) and 3 μL (final concentration: 15 μmol/L) of ATP (Sigma-Aldrich) were respectively added thereto, followed by shaking for 2 minutes and further allowing to incubate at 25° C. for 40 minutes to carry out an enzymatic reaction. It should be noted that FLT D835Y refers to an FLT3 protein with a substitution of aspartic acid 835 to tyrosine.

Then, 30 μL of an enzyme reaction stop solution (5 μg/mL Streptavidin, 0.19 μg/mL PT66-K, 30 μmol/L HEPES (pH 7.0), 150 mmol/L KF, 75 mM EDTA, 0.15% BSA, 0.075% Tween20) containing Streptavidin-Xlent (Cisbio) and Mab PT66-K (Cisbio) was added to stop the enzymatic reaction, followed by allowing to incubate at room temperature for 1 hour to carry out an antigen-antibody reaction. Thereafter, phosphorylation of the substrate peptide was measured by measuring the time-resolved fluorescence of 615 nm and 665 nm using an Envision (PerkinElmer). By taking the value obtained by dividing the fluorescence value at 665 nm by the fluorescence value at 615 nm as a measured value, taking the measured value of the well with no addition of the compound (DMSO treatment only) and addition of ATP as 0% inhibition, and taking the measured value of the well with no addition of the compound (DMSO treatment only) and no addition of ATP as 100% inhibition, a 50% inhibitory concentration (IC$_{50}$ value) of the test compound was calculated by Fit Model 205 of XLfit Ver. 5.3.1 (ID Business Solutions Limited). The results are shown in Table 2.

TABLE 2

| Compound No. | IC$_{50}$ |
|---|---|
| Reference Compound 1 | – |
| 1 | ++ |
| 2 | +++ |
| 3 | ++ |
| 4 | ++ |
| 5 | +++ |
| 6 | ++ |
| 7 | +++ |
| 8 | ++ |
| 9 | +++ |
| 10 | +++ |
| 11 | ++ |
| 12 | ++ |
| 13 | ++ |
| 14 | +++ |
| 15 | ++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |
| 31 | ++ |
| 32 | +++ |
| 33 | ++ |
| 34 | +++ |
| 35 | +++ |
| 36 | +++ |
| 37 | +++ |
| 38 | +++ |
| 39 | +++ |
| 40 | +++ |
| 41 | +++ |

In the table, the evaluation standards of an IC$_{50}$ value for an enzymatic activity of a mutant FLT3 protein are as follows.
+++: less than 1 nmol/L
++: more than or equal to 1 nmol/L and less than 10 nmol/L
+: more than or equal to 10 nmol/L and less than 100 nmol/L
–: more than or equal to 100 nmol/L

Example 2

Establishment of Mutant FLT3-Expressing 32D Cell Lines and Cell Growth Assay Using the Same Cell Lines Materials As a wild-type FLT3/FLT3 ligand-coexpressing 32D cell line (32D FLT3/FL), known cells described in Shiotsu Y, et al., Blood, Vol. 114, pp. 1607 to 1617, 2009 were used. RPMI1640 and DMEM were purchased from Life Technologies or SIGMA. The 32D cells were obtained from RIKEN Bioresource Center, and cultured in the presence of 5% CO$_2$ at 37° C. using an RPMI1640 medium containing 1 ng/mL mouse IL-3, 10% fetal bovine serum (FBS), 100 U/mL penicillin and 100 ng/mL streptomycin. The PLAT-E cells were kindly provided by Dr. Kitamura Toshio of Tokyo University and cultured in a DMEM medium containing 1 μg/mL puromycin, 10 μg/mL blasticidin S, 10% FBS, 100 U/mL penicillin and 100 ng/mL streptomycin. The pMXs-IP retroviral vector was kindly provided by Dr. Kitamura Toshio of Tokyo University (Kitamura T, et al., Exp Hamtol, Vol. 31, pp. 1007 to 1014, 2003). A pGEM-T vector, FuGENE6 and CellTiter 96 AQueous One Solution Cell Proliferation Assay were purchased from Promega Corporation.

2-2. Establishment of Cell Lines

Cell lines with the exception of 32D FLT3/FL were established as follows, according to known procedures described in Tsujimura A, et al., Int J Hematol, Vol. 92, pp. 624 to 633, 2010 and Lu Y, et al., Leukemia, Vol. 21, pp. 2246 to 2257, 2007.

(1) FLT3 D835Y, FLT3 D835V, FLT3 D835H, FLT3 D835E, FLT3 D835N, FLT3 D835Ins, FLT3 Y842C and FLT3 Y842H D835Y-, D835V-, D835H-, D835E-, D835N- and D835Ins- (I836L.D-) mutant FLT3-expressing vectors were constructed by inserting the whole length of a D835-mutant FLT3 gene sequence inserted into the pMKIT-Neo vector described in Yamamoto Y, et al., Blood, Vol. 97, pp. 2434 to 2439, 2001 into a pMXs-IP retroviral vector.

The Y842C- or Y842H-mutant FLT3-expressing vector was constructed by introducing Y842C and Y842H mutations into the C-terminal FLAG sequence-added FLT3 gene inserted into a pGEM-T vector as a template, using the primers shown below and according to the protocol of a QuikChange Site-Directed Mutagenesis Kit (Stratagene Corporation), and then inserting the whole length of a Y842-mutant FLT3 gene sequence into a pMXs-IP retroviral vector. Introduced mutations were confirmed by sequence analysis.

(2) FLT3 ITD, FLT3 ITD.D835Y, FLT3 ITD.Y842C and FLT3 ITD.Y842H

The ITD-mutant FLT3-expressing vector was constructed by introducing an ITD-mutant FLT3 gene (clone Mt2) described in Kiyoi H, et al., Leukemia, Vol. 12, pp. 1333 to 1337, 1998 into a pMXs-IP retroviral vector as a sequence having a FLAG sequence added to the C-terminal thereof.

The ITD.D835Y-mutant FLT3-expressing vector was constructed by replacing a sequence containing aspartic acid 835 cleaved by SphI, in the C-terminal FLAG sequence-added ITD-mutant FLT3 gene inserted into a pGEM-T vector, with the corresponding sequence of the C-terminal FLAG sequence-added D835Y-mutant FLT3 gene inserted into a pGEM-T vector, and then inserting the whole length of C-terminal FLAG sequence-added ITD.D835Y-mutant FLT3 sequence into a pMXs-IP retroviral vector.

The ITD.Y842C-mutant or ITD.Y842H-mutant FLT3-expressing vector was constructed by introducing Y842C and Y842H mutations into the C-terminal FLAG sequence-added ITD-mutant FLT3 gene inserted into a pGEM-T vector as a template, using the primers shown below and according to the protocol of a QuikChange Site-Directed Mutagenesis Kit (Stratagene Corporation), and then inserting the whole length of the ITD.Y842-mutant FLT3 gene into a pMXs-IP retroviral vector. Introduced mutations were confirmed by sequence analysis.

The mutant FLT3 pMXs-IP retroviral vectors prepared according to the above-mentioned procedure were introduced into PLAT-E cells by using FuGENE6, followed by culturing for 2 days, and the culture supernatant containing viruses was collected. After the virus-containing culture supernatant was added to the mouse hematopoietic precursor cell line 32D cells in the presence of 10 μg/mL polybrene, and the cells were cultured in the presence of 0.5 ng/mL mouse IL-3. Individual mutant FLT3-expressing 32D cell lines (32D FLT3 D835Y, 32D FLT3 D835V, 32D FLT3 D835H, 32D FLT3 D835E, 32D FLT3 D835N, 32D FLT3 D835Ins, 32D FLT3 Y842C, 32D FLT3 Y842H, FLT3 ITD, FLT3 ITD.D835Y, FLT3 ITD.Y842C and FLT3 ITD.Y842H) were established by the selection of cells with 4 μg/mL puromycin 2 days after viral infection operation. The expression of FLT3 was confirmed by Western blot. All of the thus established mutant FLT3-expressing 32D cell lines and FLT3/FLT3 ligand-coexpressing 32D cell lines were capable of growing in the absence of IL-3, and cultured in an RPMI1640 medium containing 10% FBS, 100 U/mL penicillin and 100 ng/mL streptomycin.

Primer sequences used for the introduction of a Y842C mutation or a Y842H mutation into an FLT3 gene Primers used for the introduction of a Y842C mutation

```
5'-CATGAGTGATTCCAACTGTGTTGTCA-3'     (SEQ ID NO: 3)

5'-TGACAACACAGTTGGAATCACTCATG-3'    (SEQ ID NO: 4)
```

Primers used for the introduction of a Y842H mutation

```
5'-CATGAGTGATTCCAACCATGTTGTCA-3'    (SEQ ID NO: 5)

5'-TGACAACATGGTTGGAATCACTCATG-3'    (SEQ ID NO: 6)
```

Mutagenesis sites are underlined.

2-3. Cell Growth Assay (1) Quizartinib (Ambit Biosciences Corporation) was used as Reference Compound 1 and Sorafenib (Bayer HealthCare Pharmaceuticals, Inc.) was used as Reference Compound 2.

The cell viability assay of FLT3/FLT3 ligand-coexpressing 32D cell lines and mutant FLT3-expressing 32D cell lines (32D FLT3 D835Y, 32D FLT3 D835V, 32D FLT3 D835H, 32D FLT3 D835E, 32D FLT3 D835N, 32D FLT3 D835Ins, 32D FLT3 Y842C and 32D FLT3 Y842H) for the compounds was carried out according to the following procedure.

Individual cells were seeded onto a 96-well plate (Becton, Dickinson and Company) at a density of 1000 to 10000 cells/well, and the cell culture was started at 37° C. in the presence of 5% $CO_2$. On the next day, the compound diluted in 3-fold common ratio was added to each well, followed by further culturing for 2 days. Then, in order to evaluate the cell viability, a CellTiter 96 AQueous One SolutionReagent was added to each well according to the Promega Corporation's protocol, followed by culturing for 1 hour. Thereafter, the absorbance (OD=492 nm) was measured using an MPR-A4i II microplate reader (Tosoh Corporation). In a case where the absorbance is insufficient, the absorbance was measured after performing the culturing for another 1 to 2 hours. By taking the well with no addition of the compound as 0% growth inhibition and taking the well with no seeding of cells as 100% growth inhibition, a 50% inhibitory concentration ($GI_{50}$ value) of the test compound was calculated by XLfit 5.3.1 software (Fit Model 205) (ID Business Solutions Limited).

The results are shown in Table 3.

TABLE 3

| | Compound 38 | Compound 39 | Compound 40 | Compound 41 | Reference Compound 1 | Reference Compound 2 |
|---|---|---|---|---|---|---|
| FLT3/FL | ++ | +++ | +++ | +++ | ++ | + |
| FLT3 D835Y | +++ | ++ | +++ | ++ | + | − |
| FLT3 D835V | +++ | ++ | +++ | ++ | − | − |
| FLT3 D835H | ++ | ++ | ++ | ++ | ++ | − |
| FLT3 D835E | ++ | +++ | +++ | ++ | ++ | + |
| FLT3 D835N | ++ | +++ | +++ | ++ | ++ | + |
| FLT3 D835Ins | ++ | +++ | +++ | ++ | ++ | + |
| FLT3 Y842C | ++ | ++ | ++ | ++ | + | − |
| FLT3 Y842H | ++ | ++ | ++ | ++ | + | − |

In the table, the evaluation standards of $GI_{50}$ values for the growth of various FLT3 protein-expressing 32D cells are as follows.
+++: less than 1 nmol/L
++: more than or equal to 1 nmol/L and less than 10 nmol/L
+: more than or equal to 10 nmol/L and less than 100 nmol/L
−: more than or equal to 100 nmol/L
Further, individual terms in the table have the following meanings.
FLT3/FL: a strain coexpressing an FLT3 protein and an FL (FLT3 ligand) protein
FLT3 D835Y: a strain expressing an FLT3 protein having a substitution of aspartic acid 835 to tyrosine
FLT3 D835V: a strain expressing an FLT3 protein having a substitution of aspartic acid 835 to valine
FLT3 D835H: a strain expressing an FLT3 protein having a substitution of aspartic acid 835 to histidine
FLT3 D835E: a strain expressing an FLT3 protein having a substitution of aspartic acid 835 to glutamic acid
FLT3 D835N: a strain expressing an FLT3 protein having a substitution of aspartic acid 835 to asparagine
FLT3 D835Ins: a strain expressing an FLT3 protein having a substitution of isoleucine 836 to leucine and aspartic acid
FLT3 Y842C: a strain expressing an FLT3 protein having a substitution of tyrosine 842 to cysteine
FLT3 Y842H: a strain expressing an FLT3 protein having a substitution of tyrosine 842 to histidine The compounds of the present invention exhibited strong cell growth inhibitory effect on the cells expressing any mutant FLT3, and the strength of the inhibitory effect was equivalent to or greater than the inhibitory effect on FLT3/FLT3 ligand-coexpressing cells.

(2)

The cell viability assay of mutant FLT3-expressing 32D cell lines (FLT3 ITD, FLT3 ITD.D835Y, FLT3 ITD.Y842C and FLT3 ITD.Y842H) for the compounds was carried out according to the procedure described in the section 2-3. (1).

The results are shown in Table 4.

TABLE 4

|  | Compound 38 |
|---|---|
| FLT3 ITD | ++ |
| FLT3 ITD•D835Y | ++ |
| FLT3 ITD•Y842C | ++ |
| FLT3 ITD•Y842H | +++ |

In the table, the evaluation standards of $GI_{50}$ values for the growth of various FLT3 protein-expressing 32D cells are the same as those in Table 2.
Further, individual terms in the table have the following meanings.
FLT3 ITD: a strain expressing an FLT3 protein having an ITD mutation
FLT3 ITD•D835Y: a strain expressing an FLT3 protein having an ITD mutation and also having a substitution of aspartic acid corresponding to the $835^{th}$ position in a wild-type FLT3 to tyrosine
FLT3 ITD•Y842C: a strain expressing an FLT3 protein having an ITD mutation and also having a substitution of tyrosine corresponding to the $842^{nd}$ position in a wild-type FLT3 to cysteine
FLT3 ITD•Y842H: a strain expressing an FLT3 protein having an ITD mutation and also having a substitution of tyrosine corresponding to the $842^{nd}$ position in a wild-type FLT3 to histidine The compounds of the present invention exhibited strong cell growth inhibitory effect on the cells expressing a mutant FLT3 having an ITD mutation and also having D835Y, Y842C or Y8421H, and the strength of the inhibitory effect was equivalent to or greater than the inhibitory effect on the cells expressing a mutant FLT3 having only an ITD mutation.

Example 3

FLT3 Phosphorylation Inhibition Assay Using HEK293T Cells Transiently Expressing Mutant FLT3

3-1. Materials

The HEK293T cell line was purchased from DS Pharma Biomedical Co., Ltd. DMEM was purchased from Life Technologies. The cell culture was carried out using a DMEM medium containing 10% fetal bovine serum (FBS) at 37° C. in the presence of 5% $CO_2$. A pcDNA3.1(+) vector and a gene transfection reagent Lipofectamine 2000 were purchased from Life Technologies. Quantification of intracellular phosphorylated FLT3 was carried out using a PathScan Phospho-FLT3(Tyr591) Chemiluminescent Sandwich ELISA Kit #7021 (Cell Signaling Technology).

3-2. Construction of Mutant FLT3-Expressing Vector

The ITD-mutant FLT3-expressing vector was constructed by incorporating an ITD-mutant FLT3 gene as a sequence having an FLAG sequence added at the C-terminal into a pcDNA3.1(+) vector.

The ITD.F691L-mutant FLT3-expressing vector was constructed by introducing an F691L mutation into an ITD-mutant FLT3-expressing vector as a template, using the primers shown below and according to the protocol of a QuikChange Site-Directed Mutagenesis Kit (Stratagene Corporation), and then inserting the whole length of the ITD.F691L-mutant FLT3 gene into a pcDNA3.1(+) vector. Introduced mutations were confirmed by sequence analysis.

Primer sequences used for the introduction of an F691L mutation

5'-CCAATTTACTTGAT<u>TTT</u>GGAATACTGTTGC-3' (SEQ ID NO: 7)

5'-GCAACAGTATTCC<u>AAA</u>ATCAAGTAAATTGG-3' (SEQ ID NO: 8)

Mutagenesis sites are underlined.

3-3. Phosphorylation Inhibition Assay in HEK293T Cells Transiently Expressing Mutant FLT3 (FLT3 ITD or FLT3 ITD.F691L)

Quizartinib (Ambit Biosciences Corporation) was used as Reference Compound 1. With respect to FLT3 ITD or FLT3 ITD.F691L which is a mutant FLT3, the genes were individually introduced into HEK293T cells by the expression vector incorporating each gene, and the assay for an inhibitory effect of compounds on FLT3 phosphorylation in the cells transiently expressing those mutant FLT3s was carried out according to the following procedure.

HEK293T cells were seeded into T75 flasks ($8 \times 10^6$ cells/flask) and cultured in the presence of 5% $CO_2$ at 37° C. for 24 hours, and the medium (15 mL) was exchanged. A Lipofectamine 2000 solution (a mixture of 160 µL of Lipofectamine reagent and 4.0 mL of OPTIMEM) and a vector solution (a mixture of 64 µg of Plasmid DNA and 4.0 mL of OPTIMEM) were mixed in a 1:1 ratio and allowed to incubate at room temperature for 20 minutes. Then, 3 mL of the resulting mixture was taken and added to HEK293T cells for which the medium was exchanged, followed by culturing in the presence of 5% $CO_2$ at 37° C. for another 24 hours. HEK293T cells into which an FLT3 ITD or FLT3 ITD.F691L gene had been introduced were seeded onto 96-well plates (#3300, Corning) at a density of each of 50000 cells/well, and precultured in the presence of 5% $CO_2$ at 37° C. for 24 hours. After the preculture, compound solutions of serial dilutions were added to each well and the cells were cultured in the presence of 5% $CO_2$ at 37° C. for 60 minutes. In order to quantify the phosphorylated FLT3 in HEK293T cells after the culture, the sample was treated using a PathScan Phospho-FLT3(Tyr591) Chemiluminescent Sandwich ELISA Kit according to the attached protocol. In summary, each well was washed with 100 µL of PBS, 50 µL of Lysis Buffer was added thereto, and then the lysate was aliquoted. The lysate was appropriately diluted, and 50 µL/well of the lysate was added to an ELISA plate onto which an FLT3 Mouse mAb had been immobilized, followed by reaction at 4° C. for 24 hours. After the reaction was completed, the supernatant of each well was discarded, followed by washing with Wash Buffer, and then Phospho-FLT3(Tyr591) Rabbit Detection Antibodies were added, followed by reaction at room temperature for 1 hour. Each well was washed and HRP-linked secondary antibodies were added thereto, followed by reaction at room temperature for 30 minutes. After the reaction was completed, each well was washed, a detection liquid (a 1:1 mixture of Luminol/Enhancer solution and Stable Peroxide Buffer) was added to each well, and the amount of light emitted at 425 nm was measured in a plate reader EnVision. By taking the well with no addition of the compound as 0% phosphorylation inhibition and taking the well with no seeding of cells as 100% phosphorylation inhibition, the 50% inhibitory concentration ($IC_{50}$ value) of the test compound was calculated by XLfit 5.3.1 software (Fit Model 205) (ID Business Solutions Limited).

The results are shown in Table 5.

TABLE 5

|  | Compound 38 | Reference Compound 1 |
| --- | --- | --- |
| FLT3 ITD | +++ | +++ |
| FLT3 ITD•F691L | ++ | − |

In the table, the evaluation standards of IC$_{50}$ values for the FLT3 phosphorylation in HEK293T cells transiently expressing mutant FLT3 are as follows.
+++: less than 10 nmol/L
++: more than or equal to 10 nmol/L and less than 30 nmol/L
+: more than or equal to 30 nmol/L and less than 90 nmol/L
−: more than or equal to 90 nmol/L
Further, individual terms in the table have the following meanings.
FLT3 ITD: a strain transiently expressing an FLT3 protein having an ITD mutation
FLT3 ITD•F691L: a strain transiently expressing an FLT3 protein having an ITD mutation and also having a substitution of phenylalanine corresponding to the 691$^{st}$ position in a wild-type FLT3 to leucine
The compounds of the present invention strongly inhibited FLT3 phosphorylation in FLT3 ITD mutation-expressing HEK293T cells at a level equivalent to or greater than that of Reference Compound 1. Further, the compounds of the present invention exhibited a strong FLT3 phosphorylation inhibitory effect even for the FLT3 ITD•F691L mutation-expressing HEK293T cells on which an FLT3 phosphorylation inhibitory effect of Reference Compound 1 is markedly attenuated.

The nitrogen-containing heterocyclic compound or the salt thereof is useful as a pharmaceutical composition for treating an FLT3 mutation-positive cancer and a mutant FLT3 inhibitor.

[Sequencing List Pretext]

SEQ ID NO.: 1 FLT3

SEQ ID NO.: 2 FLT3 substrate peptide

SEQ ID NO.: 3 Primer for Y842C mutation

SEQ ID NO.: 4 Primer for Y842C mutation

SEQ ID NO.: 5 Primer for Y842H mutation

SEQ ID NO.: 6 Primer for Y842H mutation

SEQ ID NO.: 7 Primer for F691L mutation

SEQ ID NO.: 8 Primer for F691L mutation

[Sequence List]

What is claimed is:

1. A method of treating an FLT3 mutation-positive cancer in a subject in need thereof, comprising administering to the subject a compound represented by General Formula [1]:

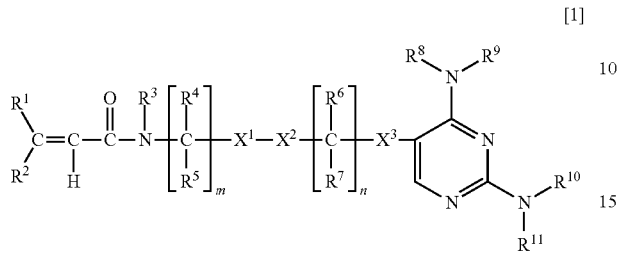

in the formula,
$R^1$ represents a hydrogen atom or a $C_{1-6}$ alkyl group which may be substituted,
$R^2$ represents a hydrogen atom, a $C_{1-6}$ alkyl group which may be substituted, a $C_{2-6}$ alkenyl group which may be substituted or a $C_{2-6}$ alkynyl group which may be substituted,
$R^3$ represents a hydrogen atom, a $C_{1-6}$ alkyl group which may be substituted, a $C_{2-6}$ alkenyl group which may be substituted or a $C_{2-6}$ alkynyl group which may be substituted,
m represents an integer of 1 to 3,
m number of $R^4$'s are the same or different and represent a hydrogen atom or a $C_{1-6}$ alkyl group which may be substituted, and one $R^4$ selected from m number of $R^4$'s together with $R^3$ may form a $C_{1-6}$ alkylene group which may be substituted,
m number of $R^5$'s are the same or different and represent a hydrogen atom or a $C_{1-6}$ alkyl group which may be substituted, a $C_{2-6}$ alkenyl group which may be substituted or a $C_{2-6}$ alkynyl group which may be substituted,
$X^1$ represents an oxygen atom, $N(R^{20})$ (in the formula, $R^{20}$ represents a hydrogen atom, a $C_{1-6}$ alkyl group which may be substituted, a $C_{2-6}$ alkenyl group which may be substituted or a $C_{2-6}$ alkynyl group which may be substituted), $C(=O)$, $C(=O)-N(R^{20})$ (in the formula, $R^{20}$ has the same meaning as defined above) or a bond,
$X^2$ represents a $C_{1-6}$ alkylene group which may be substituted, a divalent alicyclic hydrocarbon group which may be substituted or a divalent aromatic hydrocarbon group which may be substituted,
n represents an integer of 0 to 3,
n number of $R^6$'s are the same or different and represents a hydrogen atom or a $C_{1-6}$ alkyl group which may be substituted,
n number of $R^7$'s are the same or different and represents a hydrogen atom or a $C_{1-6}$ alkyl group which may be substituted,
$X^3$ represents a $C_{1-6}$ alkylene group which may be substituted, a $C_{2-6}$ alkenylene group which may be substituted, a $C_{2-6}$ alkynylene group which may be substituted or $N(R^{20})-C(=O)$ (in the formula, $R^{20}$ has the same meaning as defined above),
$R^8$ represents a hydrogen atom, a $C_{1-6}$ alkyl group which may be substituted, a $C_{2-6}$ alkenyl group which may be substituted or a $C_{2-6}$ alkynyl group which may be substituted,
$R^9$ represents a $C_{1-6}$ alkyl group which may be substituted, a $C_{2-6}$ alkenyl group which may be substituted, a $C_{2-6}$ alkynyl group which may be substituted or a $C_{3-8}$ cycloalkyl group which may be substituted,
$R^8$ and $R^9$, together with the nitrogen atom to which they are bonded, may form a cyclic amino group which may be substituted,
$R^{10}$ represents a hydrogen atom, a $C_{1-6}$ alkyl group which may be substituted, a $C_{2-6}$ alkenyl group which may be substituted or a $C_{2-6}$ alkynyl group which may be substituted, and
$R^{11}$ represents a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted or a heterocyclic group which may be substituted; or
a salt thereof.

2. The method according to claim 1, wherein $R^{10}$ is a hydrogen atom.

3. The method according to claim 1, wherein $X^1$ is $C(=O)-N(R^{20})$ (in the formula, $R^{20}$ represents a hydrogen atom, a $C_{1-6}$ alkyl group which may be substituted, a $C_{2-6}$ alkenyl group which may be substituted or a $C_{2-6}$ alkynyl group which may be substituted).

4. The method according to claim 1, wherein $X^3$ is a $C_{2-6}$ alkynylene group which may be substituted.

5. The method according to claim 1, wherein the FLT3 mutation includes a TKD mutation.

6. The method according to claim 5, wherein the TKD mutation is mutation(s) of one or plural amino acids in the amino acids 823 to 861 region in the amino acid sequence of SEQ ID NO: 1.

7. The method according to claim 6, wherein the TKD mutation is a mutation of at least one amino acid selected from the group consisting of amino acids 835, 836 and 842 in the amino acid sequence of SEQ ID NO: 1.

8. The method according to claim 7, wherein the TKD mutation is at least one selected from the group consisting of the following:
 a. a substitution of aspartic acid 835 in the amino acid sequence of SEQ ID NO: 1 to valine, tyrosine, histidine, glutamic acid or asparagine;
 b. a substitution of isoleucine 836 in the amino acid sequence of SEQ ID NO: 1 to leucine-aspartic acid; and
 c. a substitution of tyrosine 842 in the amino acid sequence of SEQ ID NO: 1 to cysteine or histidine.

9. The method according to claim 5, wherein the TKD mutation is mutation(s) of one or plural amino acids in the amino acids 604 to 822 region in the amino acid sequence of SEQ ID NO: 1.

10. The method according to claim 9, wherein the TKD mutation is a mutation of at least one amino acid selected from the group consisting of amino acids 621, 627, 676, 691 and 697 in the amino acid sequence of SEQ ID NO: 1.

11. The method according to claim 10, wherein the TKD mutation is a mutation of amino acid 691 in the amino acid sequence of SEQ ID NO: 1.

12. The method according to claim 11, wherein the mutation of amino acid 691 in the amino acid sequence of SEQ ID NO: 1 is a substitution of phenylalanine to leucine.

13. The method according to claim 5, wherein the FLT3 mutation further includes an ITD mutation.

14. A method of inhibiting a mutant FLT3 in a subject in need thereof, comprising administering to the subject the compound or the salt thereof as defined in claim 1.

15. The method according to claim 14, which inhibits mutant FLT3 containing a TKD mutation.

16. The method according to claim 15, which inhibits mutant FLT3 further containing an ITD mutation.

17. The method according to claim 14, which further inhibits wild-type FLT3.

18. The method according to claim 14, which is for treating a cancer.

* * * * *

```
                        SEQUENCE LISTING

<160> NUMBER OF SEQ ID NOS: 8

<210> SEQ ID NO 1
<211> LENGTH: 993
<212> TYPE: PRT
<213> ORGANISM: Homo sapiens

<400> SEQUENCE: 1

Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
                20                  25                  30

Ile Lys Cys Val Leu Ile Asn His Lys Asn Asn Asp Ser Ser Val Gly
            35                  40                  45

Lys Ser Ser Ser Tyr Pro Met Val Ser Glu Ser Pro Glu Asp Leu Gly
    50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220
```

-continued

```
Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
            245                 250                 255

Leu Pro Gln Leu Phe Leu Lys Val Gly Glu Pro Leu Trp Ile Arg Cys
        260                 265                 270

Lys Ala Val His Val Asn His Gly Phe Gly Leu Thr Trp Glu Leu Glu
    275                 280                 285

Asn Lys Ala Leu Glu Glu Gly Asn Tyr Phe Glu Met Ser Thr Tyr Ser
290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Glu Lys Gly Phe Ile Asn Ala
            340                 345                 350

Thr Asn Ser Ser Glu Asp Tyr Glu Ile Asp Gln Tyr Glu Glu Phe Cys
        355                 360                 365

Phe Ser Val Arg Phe Lys Ala Tyr Pro Gln Ile Arg Cys Thr Trp Thr
370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
        435                 440                 445

Gln Ala Ser Cys Phe Ser Asp Gly Tyr Pro Leu Pro Ser Trp Thr Trp
    450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
    530                 535                 540

Tyr Ala Thr Ile Gly Val Cys Leu Leu Phe Ile Val Val Leu Thr Leu
545                 550                 555                 560

Leu Ile Cys His Lys Tyr Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Pro Arg Glu
        595                 600                 605

Asn Leu Glu Phe Gly Lys Val Leu Gly Ser Gly Ala Phe Gly Lys Val
    610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
```

```
                    645                 650                 655
Ala Leu Met Ser Glu Leu Lys Met Met Thr Gln Leu Gly Ser His Glu
                660                 665                 670

Asn Ile Val Asn Leu Leu Gly Ala Cys Thr Leu Ser Gly Pro Ile Tyr
            675                 680                 685

Leu Ile Phe Glu Tyr Cys Cys Tyr Gly Asp Leu Leu Asn Tyr Leu Arg
        690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
                740                 745                 750

Ser Gly Leu His Gly Asn Ser Phe His Ser Glu Asp Glu Ile Glu Tyr
            755                 760                 765

Glu Asn Gln Lys Arg Leu Glu Glu Glu Glu Asp Leu Asn Val Leu Thr
        770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
                820                 825                 830

Ala Arg Asp Ile Met Ser Asp Ser Asn Tyr Val Val Arg Gly Asn Ala
            835                 840                 845

Arg Leu Pro Val Lys Trp Met Ala Pro Glu Ser Leu Phe Glu Gly Ile
        850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
                980                 985                 990

Ser

<210> SEQ ID NO 2
<211> LENGTH: 17
<212> TYPE: PRT
<213> ORGANISM: Artificial Sequence
<220> FEATURE:
<223> OTHER INFORMATION: FLT3 substrate peptide

<400> SEQUENCE: 2

Ala Ala Ala Ala Glu Glu Glu Glu Tyr Phe Glu Leu Val Ala Lys Lys
1               5                   10                  15
```

Lys

<210> SEQ ID NO 3
<211> LENGTH: 26
<212> TYPE: DNA
<213> ORGANISM: Artificial Sequence
<220> FEATURE:
<223> OTHER INFORMATION: Primer for Y842C mutation

<400> SEQUENCE: 3
catgagtgat tccaactgtg ttgtca    26

<210> SEQ ID NO 4
<211> LENGTH: 26
<212> TYPE: DNA
<213> ORGANISM: Artificial Sequence
<220> FEATURE:
<223> OTHER INFORMATION: Primer for Y842C mutation

<400> SEQUENCE: 4
tgacaacaca gttggaatca ctcatg    26

<210> SEQ ID NO 5
<211> LENGTH: 26
<212> TYPE: DNA
<213> ORGANISM: Artificial Sequence
<220> FEATURE:
<223> OTHER INFORMATION: Primer for Y842H mutation

<400> SEQUENCE: 5
catgagtgat tccaaccatg ttgtca    26

<210> SEQ ID NO 6
<211> LENGTH: 26
<212> TYPE: DNA
<213> ORGANISM: Artificial Sequence
<220> FEATURE:
<223> OTHER INFORMATION: Primer for Y842H mutation

<400> SEQUENCE: 6
tgacaacatg gttggaatca ctcatg    26

<210> SEQ ID NO 7
<211> LENGTH: 30
<212> TYPE: DNA
<213> ORGANISM: Artificial Sequence
<220> FEATURE:
<223> OTHER INFORMATION: Primer for F691L mutation

<400> SEQUENCE: 7
ccaatttact tgattttgga atactgttgc    30

<210> SEQ ID NO 8
<211> LENGTH: 30
<212> TYPE: DNA
<213> ORGANISM: Artificial Sequence
<220> FEATURE:
<223> OTHER INFORMATION: Primer for F691L mutation

<400> SEQUENCE: 8
gcaacagtat tccaaaatca agtaaattgg    30